(12) United States Patent
Abboud et al.

(10) Patent No.: US 7,794,454 B2
(45) Date of Patent: *Sep. 14, 2010

(54) METHOD AND DEVICE FOR EPICARDIAL ABLATION

(75) Inventors: Marwan Abboud, Pierrefonds (CA); Dan Wittenberger, Pierrefonds (CA); Daniel Nahon, Ottawa (CA); Steven G. Arless, Beaconsfield (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 1005 days.

This patent is subject to a terminal disclaimer.

(21) Appl. No.: 10/839,979

(22) Filed: May 4, 2004

(65) Prior Publication Data

US 2005/0010201 A1    Jan. 13, 2005

Related U.S. Application Data

(63) Continuation-in-part of application No. 10/657,922, filed on Sep. 9, 2003, now Pat. No. 6,942,659, which is a continuation of application No. 09/845,535, filed on Apr. 30, 2001, now Pat. No. 6,629,972, which is a continuation of application No. 09/201,071, filed on Nov. 30, 1998, now Pat. No. 6,235,019, which is a continuation-in-part of application No. 08/893,825, filed on Jul. 11, 1997, now Pat. No. 5,899,899, which is a continuation-in-part of application No. 08/807,382, filed on Feb. 27, 1997, now Pat. No. 5,899,898.

(60) Provisional application No. 60/468,490, filed on May 6, 2003.

(51) Int. Cl.
    *A61B 18/02*    (2006.01)

(52) U.S. Cl. .......................................... 606/21; 606/23

(58) Field of Classification Search ............. 606/20–26; 128/898

See application file for complete search history.

(56) References Cited

U.S. PATENT DOCUMENTS 5,147,355 A * 9/1992 Friedman et al. .............. 606/23

(Continued)

OTHER PUBLICATIONS

D'Avila, A., et al., Pericardial Anatomy for the Interventional Electrophysiologist, *J Cardiovasc Electrophysiol*, vol. 14, pp. 422-430, Apr. 2003.

(Continued)

*Primary Examiner*—Michael Peffley
(74) *Attorney, Agent, or Firm*—Christopher & Weisberg, P.A.

(57) ABSTRACT

A method is disclosed for treating heart and vascular tissue with cryotreatment. A medical instrument, such as a catheter is positioned to contact a target region of cardiac tissue such as the epicardial tissue. The instrument or catheter provided includes a cryotreatment element that has thermally-transmissive properties. The cryotreatment element may be a cryochamber for enclosing the flow of a fluid refrigerant therein. The cryotreatment element is disposed at the situs of heart or vascular tissue to be treated, usually by piercing the epicardium sac via an opening in the patient's body. A refrigerant flow within the cryochamber creates endothermic cooling with respect to the targeted heart or vascular tissue, inducing hypothermia and forming iceballs proximate the tissue. The cooling may be reversible and non-permanent, or may be permanent leading to cell death, necrosis, apoptosis and/or surgical excision or ablation of tissue.

4 Claims, 15 Drawing Sheets

U.S. PATENT DOCUMENTS

| | | | |
|---|---|---|---|
| 5,487,385 A | 1/1996 | Avitall | |
| 5,575,766 A | 11/1996 | Swartz et al. | |
| 5,673,695 A | 10/1997 | McGee et al. | |
| 5,733,280 A * | 3/1998 | Avitall | 606/23 |
| 5,868,735 A | 2/1999 | Lafontaine | |
| 5,938,660 A | 8/1999 | Swartz et al. | |
| 5,964,778 A | 10/1999 | Fugoso et al. | |
| 5,972,013 A | 10/1999 | Schmidt | |
| 5,980,486 A | 11/1999 | Enger | |
| 6,012,457 A | 1/2000 | Lesh | |
| 6,036,697 A | 3/2000 | DiCaprio | |
| 6,161,543 A | 12/2000 | Cox et al. | |
| 6,164,283 A | 12/2000 | Lesh | |
| 6,179,827 B1 | 1/2001 | Davis | |
| 6,214,002 B1 | 4/2001 | Fleischman et al. | |
| 6,231,518 B1 | 5/2001 | Grabek et al. | |
| 6,233,491 B1 | 5/2001 | Kordis et al. | |
| 6,237,605 B1 | 5/2001 | Vaska et al. | |
| 6,241,754 B1 | 6/2001 | Swanson et al. | |
| 6,245,064 B1 | 6/2001 | Lesh | |
| 6,305,378 B1 | 10/2001 | Lesh | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,355,029 B1 | 3/2002 | Joye et al. | |
| 6,416,511 B1 | 7/2002 | Lesh et al. | |
| 6,474,340 B1 | 11/2002 | Vaska et al. | |
| 6,484,727 B1 | 11/2002 | Vaska et al. | |
| 6,502,576 B1 | 1/2003 | Lesh | |
| 6,514,245 B1 | 2/2003 | Williams et al. | |
| 6,517,536 B2 | 2/2003 | Hooven et al. | |
| 6,527,768 B2 | 3/2003 | Berube | |
| 6,546,935 B2 | 4/2003 | Hooven | |
| 6,569,082 B1 | 5/2003 | Chin | |
| 6,592,552 B1 | 7/2003 | Schmidt | |
| 6,602,276 B2 * | 8/2003 | Dobak et al. | 607/105 |
| 6,645,202 B1 | 11/2003 | Pless et al. | |
| 6,648,878 B2 | 11/2003 | Lafontaine | |
| 6,648,879 B2 | 11/2003 | Joye et al. | |
| 6,652,515 B1 | 11/2003 | Maguire et al. | |
| 6,666,858 B2 * | 12/2003 | Lafontaine | 606/21 |
| 6,685,732 B2 | 2/2004 | Kramer | |
| 6,689,128 B2 * | 2/2004 | Sliwa et al. | 606/41 |
| 6,695,769 B2 | 2/2004 | French et al. | |
| 6,701,931 B2 | 3/2004 | Sliwa, Jr. et al. | |
| 6,719,755 B2 | 4/2004 | Sliwa, Jr. et al. | |
| 6,730,077 B2 * | 5/2004 | Carroll et al. | 606/21 |
| 6,989,009 B2 | 1/2006 | Lafontaine | |
| 2002/0069884 A1 * | 6/2002 | Boyd et al. | 128/898 |
| 2002/0183730 A1 * | 12/2002 | Reu et al. | 606/21 |
| 2004/0220558 A1 * | 11/2004 | Reu et al. | 606/21 |
| 2005/0027289 A1 * | 2/2005 | Castellano et al. | 606/21 |
| 2006/0004351 A1 * | 1/2006 | Arless et al. | 606/21 |

OTHER PUBLICATIONS

Anonymous Author, Flex 10, *Afx Microwave Beating Heart Ablation System*, Products Page, http://www.afx-inc.com/flex10.htm, visited May 4, 2004.

Saltman, A.E., et al., A Completely Endoscopic Approach to Microwave Ablation for Atrial Fibrillation, *The Heart Surgery Forum*, (#2003-11333; Jan. 13, 2003) 6(3): E38-41.

* cited by examiner

|  | PRESS. [psi] | TEMPERATURE [°C] | | | |
| --- | --- | --- | --- | --- | --- |
|  |  | TIP | RING1 | RING2 | RING3 |
| Test I |  |  |  |  |  |
|  | 230 | -45 | 6 | 16 | 13 |
|  | 250 | -45 | -36 | 3 | 1 |
|  | 270 | -43 | -43 | -19 | -20 |
|  | 290 | -40 | -47 | -23 | -22 |
|  | 310 | -40 | -47 | -32 | -25 |
|  | 330 | -39 | -47 | -38 | -27 |
|  | 350 | -39 | -47 | -47 | -31 |
|  | 370 | -40 | -47 | -48 | -45 |
|  | 390 | -39 | -47 | -48 | -49 |
|  | 410 | -36 | -46 | -47 | -49 |
|  | 430 | -36 | -46 | -48 | -49 |
| Test II |  |  |  |  |  |
|  | 235 | -50 |  |  |  |
|  | 275 | -51 | -52 | -4 | 6 |
|  | 300 | -44 | -50 | -53 | -2 |
|  | 325 | -43 | -51 | -52 | -24 |
|  | 350 | -43 | -50 | -51 | -33 |
|  | 375 | -42 | -49 | -50 | -52 |
|  | 400 | -40 | -49 | -50 | -53 |
|  | 425 | -39 | -48 | -49 | -51 |
|  | 449 | -37 | -47 | -48 | -50 |
| Test III |  |  |  |  |  |
|  | 235 | -48 | -40 | 20 | 25 |
|  | 275 | -48 | -42 | 0 | 5 |
|  | 300 | -47 | -47 | -38 | -8 |
|  | 325 | -45 | -49 | -44 | -25 |
|  | 350 | -42 | -51 | -51 | -35 |
|  | 375 | -41 | -49 | -52 | -51 |
|  | 400 | -38 | -47 | -48 | -52 |
|  | 425 | -38 | -47 | -48 | -53 |
|  | 449 | -36 | -47 | -47 | -50 |

FIG. 19

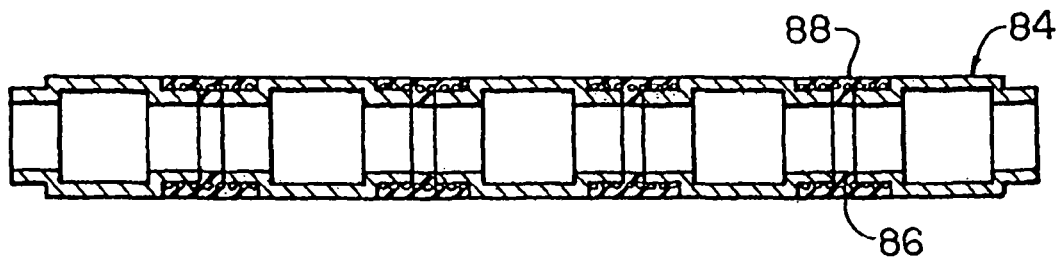
FIG. 20
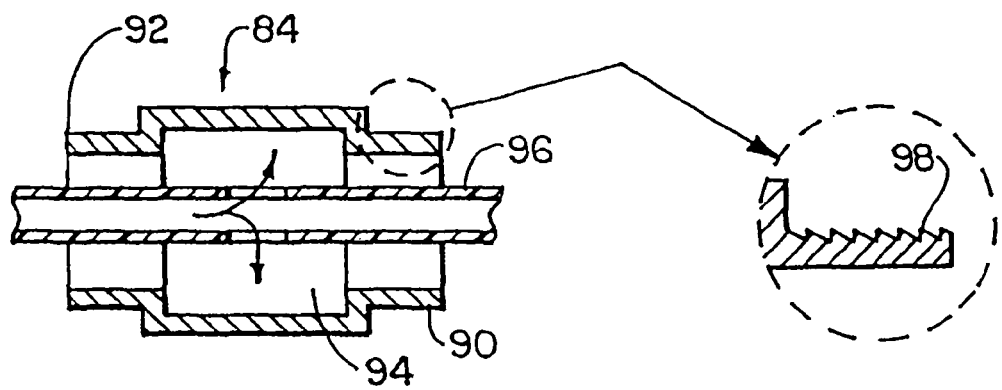
FIG. 21
FIG. 22
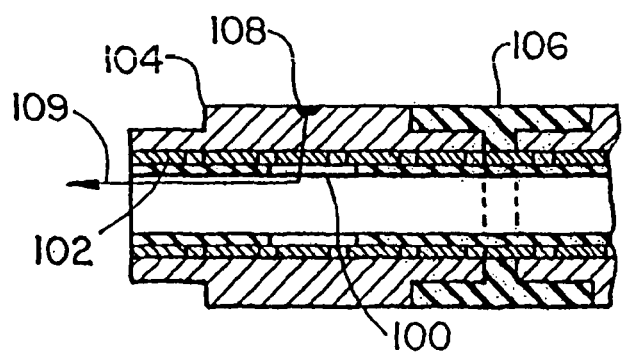
FIG. 23

METHOD AND DEVICE FOR EPICARDIAL ABLATION

CROSS-REFERENCE TO RELATED APPLICATION

This application is related to and claims priority to U.S. Provisional Patent Application Ser. No. 60/468,490, filed May 6, 2003, entitled METHOD AND DEVICE FOR EPICARDIAL ABLATION, and is a continuation-in-part of application Ser. No. 10/657,922, filed Sep. 9, 2003, entitled CRYOSURGICAL CATHETER, now issued U.S. Pat. No. 6,942,659, which is a continuation of application Ser. No. 09/845,535, filed Apr. 30, 2001, entitled CRYOSURGICAL CATHETER, now issued U.S. Pat. No. 6,629,972, which Application is a continuation of U.S. patent application Ser. No. 09/201,071, filed Nov. 30, 1998, now issued U.S. Pat. No. 6,235,019, which is a continuation-in-part of U.S. patent application Ser. No. 08/893,825, filed Jul. 11, 1997, now issued U.S. Pat. No. 5,899,899, which is a continuation-in-part of U.S. patent application Ser. No. 08/807,382, filed Feb. 27, 1997, now issued U.S. Pat. No. 5,899,898, the entirety of all of which is incorporated herein by reference.

STATEMENT REGARDING FEDERALLY SPONSORED RESEARCH OR DEVELOPMENT n/a

FIELD OF THE INVENTION

The present invention relates generally to the diagnosis and treatment of heart and vascular tissue, and more particularly, to a method for cryotreatment of epicardial and vascular tissue.

BACKGROUND OF THE INVENTION

Electrophysiological procedures require recording of cardiac electrical activity. An electrophysiology study may provide determination of the location and treatment of arrhythmias including atrial fibrillation, atrial flutter, ventricular arrhythmias, atrial-ventricular (AV) conduction delays or blocks, and paroxysmal supraventricular tachycardia (PSVT).

Two significant heart rhythm disorders amenable to electrophysiology technology are atrial fibrillation (AF) and ventricular tachycardia (VT). Treatment of AF and VT via electrophysiology methods include diagnosing the source of the arrhythmia by locating its origin ("mapping") and restoring normal heart rhythms by isolating or destroying the arrhythmia causing sites ("ablation").

One traditional AF surgical procedure, known as the "Maze" procedure, required a surgeon to craft several slices through the wall of the atrium with a scalpel so as to create a conductive scar pattern. While effective in treating AF, this procedure is complicated to perform, highly invasive, and typically associated with bleeding complications resulting in extended hospitalization.

Today, as an alternative to open-heart surgery, many medical procedures are performed using minimally invasive surgical techniques, wherein one or more slender implements are inserted through one or more small incisions into a patient's body. For those procedures using ablation, the surgical implement can include a rigid or flexible structure having an ablation device at or near its distal end that is placed adjacent to the tissue to be ablated. Ablation is typically used to destroy arrhythmia-causing tissue by burning, freezing or surgical removal. Some techniques involve positioning a catheter inside the heart at an arrhythmogenic focus or conduction defect and thermally ablating the heart tissue.

Presently, radio frequency (RF) energy is a popular method for ablation; but it has the potential of destroying healthy coronary structures and creating stenosis when a lesion is created on an artery or vein. Another drawback to the use of RF is that once a physician commences to burn the subject tissue, the procedure is absolute. Once the target focus site is identified, the surgical excision is performed and the procedure is final. No correction is made for mapping errors, nor does it allow for continuous or "progressive" monitoring of the ablation process. Known ablation tools do not allow for enhanced mapping in conjunction with, and as an integral part of, the ablation process.

Therefore, it is desirable to have a method for diagnosing and treating heart and vascular tissue that is minimally invasive and does not cause peripheral damage to healthy tissue and allows for corrections for mapping errors. Furthermore, it is desirable to provide an ablation method to diagnose and treat heart and vascular tissue that is progressive, and may be used in conjunction with known mapping techniques to allow for continuous mapping during the ablation process.

SUMMARY OF THE INVENTION

The present invention provides a cryogenic catheter having an elongate outer member and a plurality of inner members disposed within the elongate outer member. The inner members have a plurality of controllable openings formed thereon for the selective release of cryogenic fluid. A plurality of electrode members are disposed on an external surface of the outer member. The inner members may be positioned in a staggered configuration or alternatively at least one inner member may be disposed within another inner member. In such a configuration, one of the inner members may be slidable or rotatable to the other.

In addition, a method is disclosed for cryotreatment of a target region of heart tissue including the steps of inserting a medical instrument having a thermally-transmissive segment into the patient, guiding the instrument to a predetermined portion of the patient's cardiac tissue and positioning the thermally-transmissive segment adjacent the predetermined portion of the patient's epicardial tissue to be ablated, directing a flow of cryogenic fluid to the tip portion, effecting a cooling of the cardiac tissue adjacent the thermally-transmissive segment, and removing the fluid from the thermally-transmissive segment.

Another method is disclosed for cryotreatment of tissue outside a blood vessel including inserting a medical instrument having a thermally-transmissive segment into the patient's body, guiding the instrument to a predetermined portion of the patient's body and positioning the thermally-transmissive segment adjacent tissue of the blood vessel to be ablated, directing a flow of cryogenic fluid to the thermally-transmissive segment, effecting a cooling of the cryogenic fluid adjacent the thermally-transmissive segment, and removing the fluid from the thermally-transmissive segment.

Finally, a method is disclosed for cryotreatment of heart tissue including the steps of providing a medical instrument having a flexible body having at least one lumen, proximal and distal end portions, the distal end portion enclosing a thermally transmissive cryochamber in fluid communication with the at least one lumen, positioning the instrument to dispose the cryochamber proximate the target region of heart tissue, injecting a refrigerant fluid flow into the at least one lumen in the instrument body, and expanding the refrigerant fluid flow inside the cryochamber, wherein the step of positioning the instrument to dispose the cryochamber proximate the target region of heart tissue includes percutaneously inserting the distal end portion of the instrument through the pericardium for accessing the target region of heart tissue, and advancing the instrument through the pericardium to dispose the cryochamber proximate the target region of heart tissue.

DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 19 is a table illustrating cooling performance of a catheter in accordance with the invention;

FIG. 20 is a sectional view of another catheter embodiment;

FIG. 21 is a sectional view of a portion of the catheter of FIG. 20;

FIG. 22 is a detailed view of an area of the catheter portion illustrated in FIG. 21;

FIG. 23 is an illustration of yet another catheter embodiment;

DETAILED DESCRIPTION OF THE INVENTION

Figure 1:
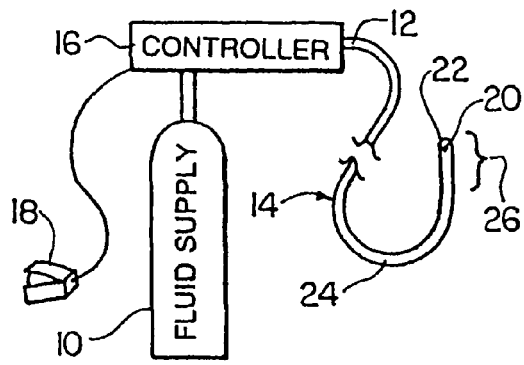
FIG. 1 is a schematic illustration of an embodiment of a cryosurgical system in accordance with the invention.

FIG. 1 is a schematic illustration of a cryosurgical system in accordance with the invention. The system includes a supply of cryogenic or cooling fluid 10 in communication with the proximal end 12 of a flexible catheter 14. A fluid controller 16 is interposed or in-line between the cryogenic fluid supply 10 and the catheter 14 for regulating the flow of cryogenic fluid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals. In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example a temperature sensor can be placed at a point proximate the distal end 22 of the catheter and other temperature sensors 20 can be placed at spaced intervals between the distal end of the catheter and another point that is between the distal end and the proximal end.

The cryogenic fluid can be in a liquid or a gas state. An extremely low temperature can be achieved within the catheter, and more particularly on the surface of the catheter by cooling the fluid to a predetermined temperature prior to its introduction into the catheter, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50—50 mixture of difluoromethane & pentafluoroethane sold by Allied Signal), and CFC's such as DuPont's Freon. Exemplary gasses include nitrous oxide, and carbon dioxide.

The catheter 14 includes a flexible member 24 having a thermally-transmissive region 26 and a fluid path through the flexible member to the thermally-transmissive region. A fluid path is also provided from the thermally-transmissive region to a point external to the catheter, such as the proximal end 12. Although described in greater detail below, exemplary fluid paths can be one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat.

For example, a metal structure exposed (directly or indirectly) to the cryogenic fluid path is considered a thermally-transmissive region 26 even if an adjacent polymeric or latex catheter portion also permits heat transfer, but to a much lesser extent than the metal. Thus, the thermally-transmissive region 26 can be viewed as a relative term to compare the heat transfer characteristics of different catheter regions or structures.

Furthermore, while the thermally-transmissive region 26 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process without having to relocate the catheter one or more times or drag it across tissue. Additional details of the thermally-transmissive region 26 and the thermal transfer process are described in greater detail below.

In exemplary embodiments of the invention, the thermally-transmissive region 26 of the catheter 14 is deformable. An exemplary deformation is from a linear configuration to an arcuate configuration and is accomplished using mechanical and/or electrical devices known to those skilled in the art. For example, a wall portion of the flexible member 24 can include a metal braid to make the catheter torqueable for overall catheter steering and placement. Additionally, a cord, wire or cable can be incorporated with, or inserted into, the catheter for deformation of the thermally transmissive region 26.

Figure 2:
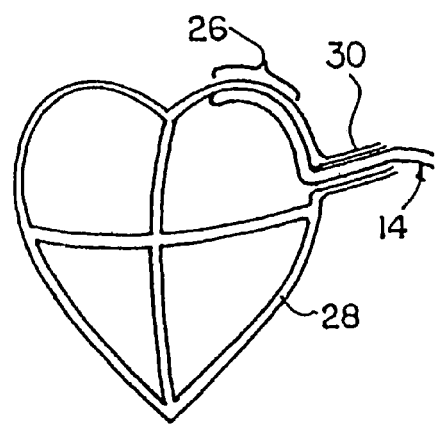
FIG. 2 is a schematic depiction of the chambers of the heart showing placement of the catheter of FIG. 1.

The cryogenic system of FIG. 1 is better understood with reference to its use in an operative procedure as shown in FIG. 2. Following the determination of a proposed lesion site within a heart chamber 28, for example, the catheter 14 is directed through a blood vessel 30 to a region within the heart, such as an atrial or ventricular chamber, where the lesion will be made. The thermally-transmissive region 26 is placed proximate to the tissue to be ablated. The thermally-transmissive region of the catheter may be deformed to conform to the curvature of the tissue before, during, or after placement against the tissue. The controller 16 allows or causes cryogenic fluid to flow from the cryogenic fluid supply 10 to the fluid path in the catheter 14 and thence to the thermally-transmissive region 26 to ablate the desired area or to cold map along the same tissue area. In one embodiment (e.g., FIG. 12) a first conduit is concentric within a second conduit and cooling fluid travels to a thermally-transmissive region proximate a closed distal end of the catheter through a first conduit (fluid path) and is exhausted from the catheter through the second conduit (fluid path).

Having described the function of the cryogenic catheter 14 and its use in a system context, several exemplary embodiments of the thermally-transmissive region 26 of the catheter are now described in greater detail. FIGS. 3, 4, 5, 12-16 and 18 illustrate embodiments of the catheter, or portions thereof, having two or more thermally-transmissive segments in a spaced-apart relationship. Each of the illustrated catheters includes a closed tip 32 that can include a thermally-transmissive material.

Figure 3:
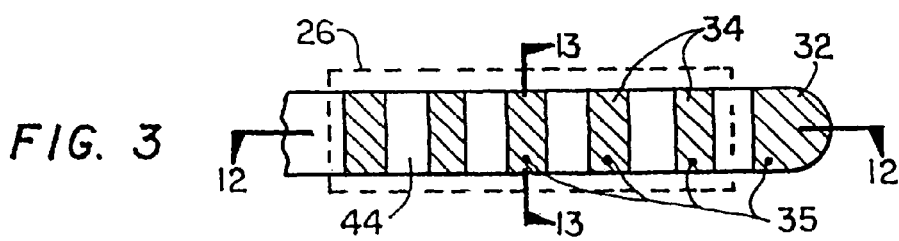
FIG. 3 illustrates the tip region of one embodiment of the catheter in accordance with the invention.
Figure 13:
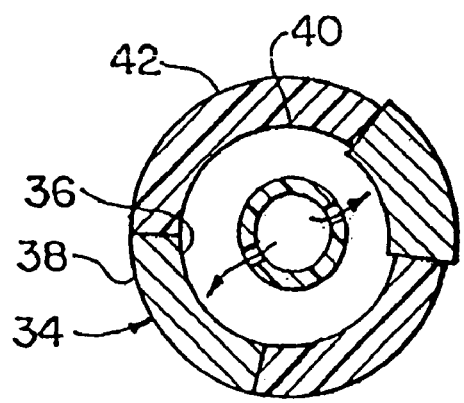
FIG. 13 is a sectional view of the catheter of FIG. 3 taken along line 13-13.
Figure 14:
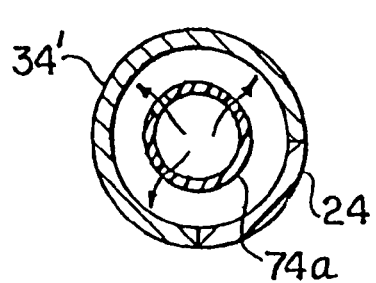
FIGS. 14-16 are sectional views of additional catheter embodiments.
Figure 15:
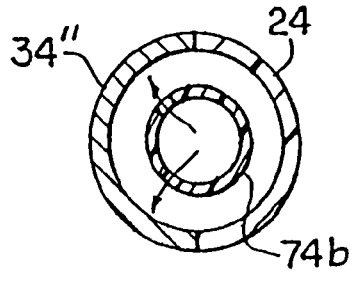
Figure 16:
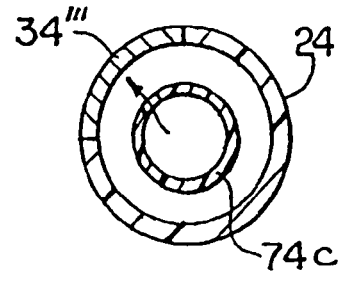

Referring specifically to the embodiment depicted in FIG. 3, multiple thermally-transmissive elements 34 are integral with a distal portion of a catheter. Each of the thermally-transmissive elements 34 includes a first side or face 36 (shown in FIGS. 12 and 13) exposed to a cryogenic fluid path and cryogenic fluid (shown by arrows) and a second side or face 38 exposed to points exterior to the catheter. As shown in FIG. 13, the first side 36 and/or second side 38 of any or all of the thermally-transmissive elements 34 can be substantially flush with, recessed below, or protruding from the inner surface 40 and outer surface 42 of a portion of the catheter. The thermally-transmissive elements 34 are separated by flexible portions of material 44 than can range from slightly less thermally-transmissive than the adjacent thermally-transmissive elements to substantially less thermally-transmissive than the adjacent elements. In the illustrated embodiment of FIG. 3, the thermally-transmissive elements 34 are annular, cylindrical elements which are made of gold-plated copper or bronze. Thermocouples 35 can be associated with one or more of the elements 34 and the tip 32. The thermally-transmissive elements 34 can be completely exposed, embedded, or a combination thereof along the full 360° of the catheter's circumference. In certain applications the thermally-transmissive elements traverse or define less than 360° of the catheter's circumference as shown in FIGS. 14-16 and as described below. The longitudinal width of each thermally-transmissive element 34, the spacing between elements, the material thickness, and the material composition are matched with a selected cryogenic fluid, one or more cryogenic fluid delivery locations within the catheter and fluid delivery pressure to produce overlapping cold regions which produce a linear lesion.

Figure 4:
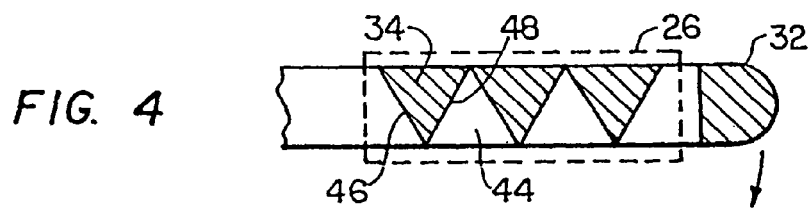
FIG. 4 illustrates an alternative embodiment of the catheter of FIG. 3.

The embodiment illustrated in FIG. 4 is substantially identical to the embodiment of FIG. 3, however, at least one of the thermally-transmissive elements 34 includes a first open end 46 that defines a first plane and a second open end 48 that defines a second plane, wherein the first and second planes intersect to give the annular elements a wedge-like appearance. Such a configuration permits adjacent thermally-transmissive elements 34 to be positioned very closely together, but it can limit the possibilities for deforming the thermally-transmissive region 26, which, in this embodiment, is flexible in the direction indicated by the arrow.

Figure 5:
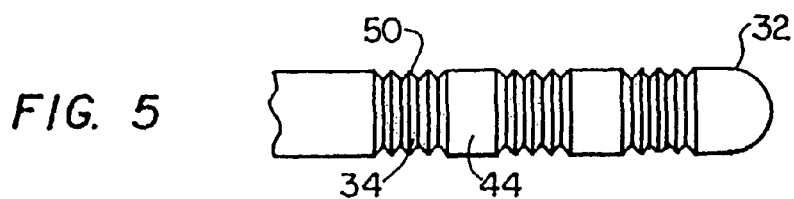
FIG. 5 illustrates yet another embodiment of the catheter.

With respect to the embodiments shown in both FIGS. 3 and 4, the thermally-transmissive elements 34 are substantially rigid and are separated and/or joined by a flexible material 44. However, in other embodiments the thermally-transmissive elements 34 are flexible and are interdigitated with either rigid or flexible segments. FIG. 5, for example, illustrates an embodiment of the cryogenic catheter having three thermally-transmissive elements 34 that are flexible. The flexibility is provided by a folded or bellows-like structure 50. In addition to being shapable, a metal bellows can have enough stiffness to retain a selected shape after a deforming or bending step.

Figure 6:
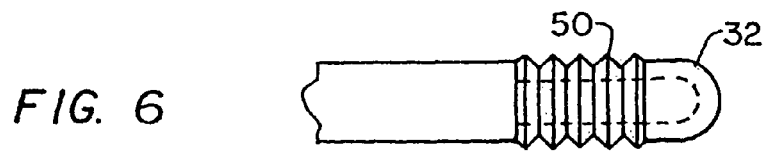
FIG. 6 illustrates a deformable tip for a catheter.

Instead of, or in addition to, flexible, thermally-transmissive elements 34 and/or flexible material 44 between elements, the distal tip 32 (or a portion thereof) can be deformable. For example, FIG. 6 illustrates a tip 32 having thermally-transmissive, flexible, bellows 50.

Figure 7:
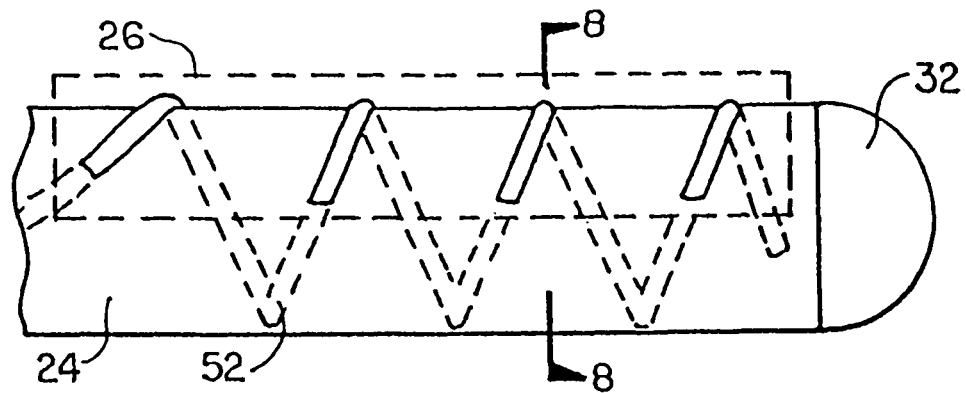
FIG. 7 illustrates yet another embodiment of the catheter.
Figure 8:
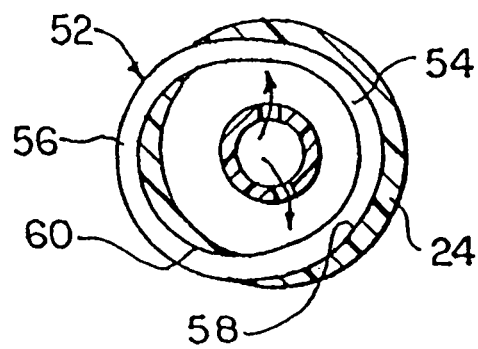
FIG. 8 is a sectional view of the catheter of FIG. 7 taken along line 8-8.

Referring now to FIGS. 7-10, a different approach is shown for providing multiple thermally-transmissive segments in a spaced-apart relationship. FIG. 7 illustrates a catheter embodiment having an elongate, thermally-transmissive region 26 that includes a helical coil 52 at least partially embedded in the flexible member 24. As shown in FIG. 8, at least a first portion 54 of the helical coil 52 is exposed to a fluid path within the flexible member 24 and a second portion 56 of the helical coil is exposed to the exterior of the flexible member. As described above with respect to FIG. 13, the first portion 54 of the coil can be substantially flush with, recessed below, or protruding from an inner surface 58 of the flexible member 24. Similarly, the second portion 56 of the coil 52 can be substantially flush with, recessed below, or protruding from an outer surface 60 of the flexible member 24.

In the embodiment of FIG. 8, the second portion 56 of the coil 52 is exposed along only a portion of the outer circumference of the flexible member 24 to define a longitudinally-elongate, thermally-transmissive region 26. This configuration can be provided by eccentrically mating the helical coil 52 to the catheter so that the longitudinal axis of the coil and the longitudinal axis of the catheter are substantially parallel. The eccentric positioning of the coil 52 provides excellent cooling performance because the surface area available for thermal exchange between the first portion 54 of coil and the cryogenic fluid is greater than the surface area available for thermal exchange between the second portion 56 of the coil and adjacent tissue where cooling power is delivered by each exposed coil portion to provide a linear lesion.

Figure 9:
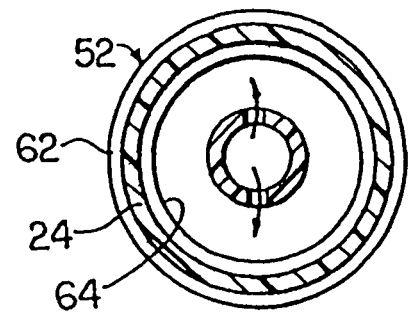
FIG. 9 is a sectional view of an alternative embodiment of the linear ablation catheter illustrated in FIG. 7.

Referring now to FIG. 9, an alternative embodiment is shown wherein a first portion 62 of the coil 52 is exposed around the entire circumference of the flexible member 24, and a second portion 64 is exposed to a fluid path around the inner surface of the flexible member 24. This is achieved by having the longitudinal axis of the helical coil 52 co-axial with the longitudinal axis of the catheter.

Figure 10:
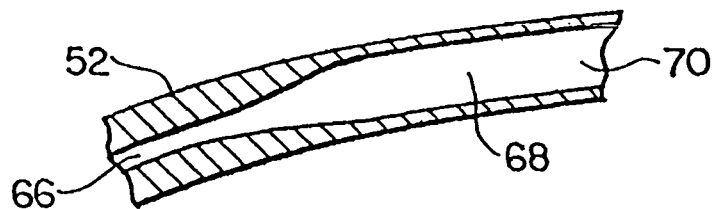
FIG. 10 illustrates an expansion chamber within a portion of a helical coil.

In the embodiments illustrated in FIGS. 7-9, the coil 52 is solid. However, in other embodiments the coil can be an elongate, hollow, gas expansion chamber. For example, FIG. 10 illustrates a portion of a helical coil 52 that includes a passage that defines at least a portion of a fluid path through a flexible member of the catheter. The coil 52 defines a first fluid path diameter at a fluid entry point 66 and a second fluid path diameter that is greater than the first fluid path diameter at a gas expansion or boiling location 68. Gas escaping from a fluid exit point 70 can be exhausted through an open central region of the coil and/or another passage through the flexible member 24.

Figure 11:
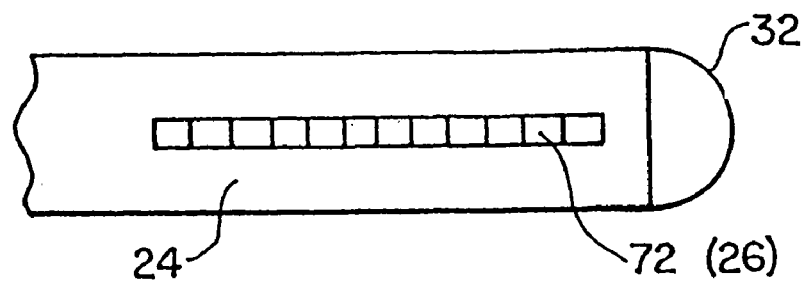
FIG. 11 illustrates a portion of a catheter having an elongate, thermally-transmissive strip.

FIG. 11 illustrates an embodiment of the catheter wherein a continuous, elongate, thermally-transmissive strip 72 is longitudinally integrated with a flexible member 24. The strip can include a bellows-like structure. As described above with respect to other embodiments, a first portion of the strip can be substantially flush with, recessed below, or protrude from the outer surface of the flexible member. Similarly, a second portion of the strip can be substantially flush with, recessed below, or protrude from an inner surface of the flexible member.

Figure 12:
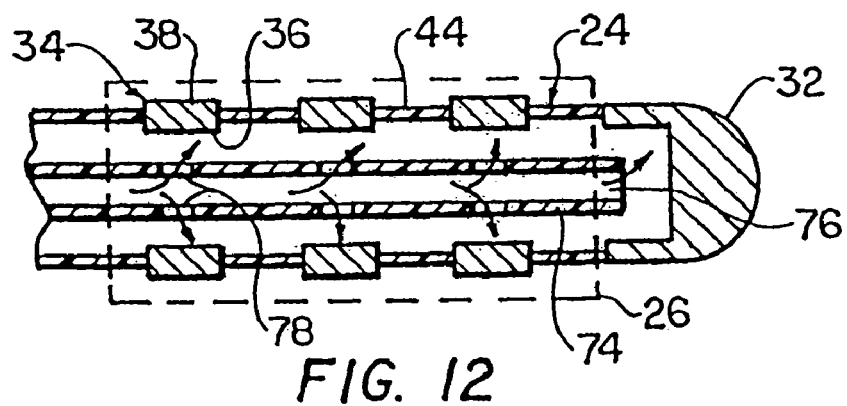
FIG. 12 is a sectional view of the catheter of FIG. 3 taken along line 12-12.

Referring now to FIG. 12, an embodiment of the catheter is illustrated having a second or inner flexible member 74 within a lumen of first or outer flexible member 24, wherein the second flexible member defines a fluid path to the thermally-transmissive region 26. The inner member 74 can include a single opening 76 at or near the tip 32. Cryogenic fluid is expelled from the opening 76 and returns to the proximal end of the catheter along a fluid path defined by the outer wall of the inner member 74 and the inner wall of the outer member 24. This fluid path configuration is also partially illustrated in FIGS. 8, 9, and 13. Alternatively, as also shown in FIG. 12, the inner member 74 can be provided with multiple openings 78 proximate to and/or aligned with the inner face of one or more thermally-transmissive elements 34 to achieve more uniform cooling across the entire elongate, thermally-transmissive region 26.

Referring now to FIGS. 14-16, sectional views of catheter embodiments are illustrated to show alternative configurations for thermally-transmissive elements. The previously described thermally-transmissive elements 34 are arcuate and form complete and continuous 360 degree structures that traverse the complete circumference of the catheter, notwithstanding being flush with, depressed below, or raised above the outermost surface of the flexible member 24. However, the arcuate elements 34', 34", and 34''' illustrated in FIGS. 14-16, respectively, traverse less than 360 degrees of the circumference of the first flexible member and do not form complete loops. For example, in FIG. 14, element 34' defines an approximately 270 degree arc. In FIG. 15 the thermally-transmissive element 34" defines an approximately 180 degree arc; and in FIG. 16, the thermally-transmissive element 34''' defines an approximately 90 degree arc. A catheter can include combinations of element types, such as a complete ring or loop element, a 270 degree element and a 180 degree element as desired to define a thermally transmissive region. In addition to the having applicability with respect to rigid thermally-transmissive elements, the bellows-like elements can also be less than 360 degrees.

The less than 360 degree arcuate elements provide unique functional benefits with respect to thermal transfer and flexibility of the thermally-transmissive region. For example, because the portion of the catheter between the opposing ends of element 34', 34", 34''' does not include a rigid structure, but rather only the resilient material of flexible member 24, the thermally-transmissive region of the catheter can be more tightly curved (gap between ends inward and element facing outward) than it could with complete 360 degree structures, especially if the elements are relatively long longitudinally.

The inner member 74 can be adapted to direct cooling fluid at only the thermally transmissive element(s) and the shape and/or the number of openings for cooling fluid can be configured differently depending on the length of the arc defined by the thermally-transmissive element(s). For example, FIG. 14 illustrates an embodiment of the inner member having three openings opposing the thermally transmissive element 34'; FIG. 15 illustrates two openings for a smaller arc; and FIG. 16 discloses a single opening for an even smaller arc.

Another advantage to providing one or more thermally-transmissive elements that have a less than 360 degree configuration is that limiting the span of the elements to a desired lesion width, or somewhat greater than a desired lesion width, reduces the thermal load on the system and/or permits colder temperatures to be achieved than with respect to a complete 360 degree structure. Unnecessary and perhaps undesirable cooling does not occur at any other location along the catheter except at an elongate region of predetermined width. A similar effect can also be achieved by providing a non-circular 360 degree element or by eccentrically mounting a circular 360 degree element with respect to the flexible member, wherein a portion of the 360 degree element is embedded within the wall of the flexible member or otherwise insulated from the cryogenic fluid path in a manner similar to that shown in FIG. 8.

Figure 17:
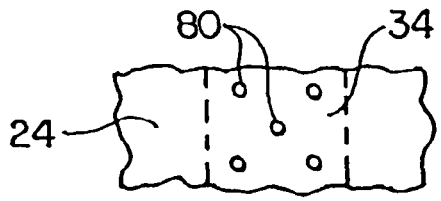
FIG. 17 illustrates an inner face of a flexible catheter member.

Referring now to FIG. 17, a portion of the inner face of an outer flexible member showing in an exemplary embodiment, thermal transfer pins 80 protruding from the inner face of a thermally-transmissive element 34. The pins permit thermal transfer through the flexible member 24. As with the other features of the invention, the pins are equally suitable for complete 360 degree element structures or less than 360 degree structures. Although only pins are shown on any geometric or surface means to increase heat transfer including but not limited to pins, irregularities, channels or surface modifications may be used.

Figure 18:
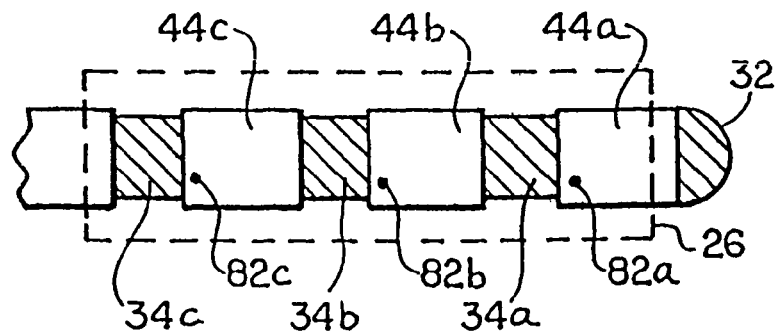
FIG. 18 depicts yet another embodiment of a catheter in accordance with the invention.

Referring now to FIG. 18, yet another embodiment of the catheter is shown wherein rigid metal rings 34a-c are interdigitated with flexible segments 44a-c to define a first flexible member and a thermally-transmissive region approximately one inch in length. A second flexible member is concentric within the first flexible member and has an outlet for cryogenic fluid at its distal end. Thermocouples 82a-c can be associated with one or more of the rings 34a-c.

It has been described above how the thermal loading of a cooling system can be reduced by providing thermally-transmissive elements that span less than 360 degrees. However, the thermal loading can also be reduced by sequentially cooling the thermally-transmissive region. One way to sequentially cool is to modulate the pressure of the cooling fluid along the fluid path through the flexible member. This modulation can be performed by the fluid controller which can be programmed to increase and decrease the pressure of the fluid by predetermined pressure increments over predetermined time intervals. When the cryogenic fluid is a liquid that provides cooling by changing phase from liquid to gas, the change of pressure alters the physical location along the fluid path where the phase change takes place and concomitantly changes the point of coldest temperature along the thermally-transmissive region. Thus, varying the pressure of the fluid can provide a moving ice-formation "front" along the catheter, enabling the creation of a linear lesion.

Therefore, a method of forming an elongate tissue lesion can include the following steps using any of the above described catheters having an elongate, thermally-transmissive region. In a first step a cryogenic fluid is introduced into the flexible member at a first predetermined pressure. Next, the pressure of the cryogenic fluid is incrementally increased within the flexible member until a second predetermined pressure is achieved. Similarly, the pressure of the cryogenic fluid within the flexible member can be decreased incrementally from the second predetermined pressure to the first predetermined pressure, wherein the steps of incrementally increasing and decreasing the pressure define a thermal cycle. Typically, from one to eight thermal cycles are required to achieve a desired therapeutic effect. In an exemplary method, about ten increments of about five seconds in duration are selected and pressure is increased by about 20 to 40 pounds per square inch in each increment. Thus, using this method an elongate lesion can be created in less than 20 minutes.

FIG. 19 is a table that illustrates sequential cooling in a catheter as described above having a thermally-transmissive region that includes a tip and three elements or rings. The table illustrates three tests conducted in a still bath at 37° C., using AZ-20 as the cryogenic fluid. Associated with each pressure increment are measured temperatures at the tip, first ring, second ring, and third ring. The shaded region illustrates the sequential movement of a target temperature range (upper −40's to low −50's) in response to a change in pressure. Although values are only provided for three rings, a similar effect and pattern is obtained with more than three rings or elements.

Turning now to FIG. 20, a thermally-transmissive portion of another embodiment of a medical device or structure such as a catheter is illustrated in a sectional view. The structure can include an inner passage or lumen as described above with respect to other embodiments, but which is not shown in this illustration for purposes of clarity. Thus, the illustrated portion is the outer passage or lumen that defines an elongate ablation region. Thermally-transmissive elements 84, such as gold plated copper, are joined to adjacent elements by resilient connecting elements 86, such as a stainless steel springs welded to the ends of the elements 84. A resilient bio-compatible material 88 covers the connecting elements 86 and the interstices between adjacent thermally-transmissive elements. In an exemplary embodiment, the material 88 is vulcanized silicone. It should be noted in the illustration that the surface of the elements 84 is contiguous and co-planar with the material 88 to provide a smooth outer surface.

FIG. 21 illustrates a single thermally-transmissive element 84 having reduced diameter ends 90 and 92. The wider central portion 94 provides an expansion chamber for gas (shown by arrows) exiting an apertured inner passage 96. FIG. 22 shows additional detail of the end 90 of the element 84. The end 90 is textured, such as by providing serrations 98, to provide a good adhesion surface for the material 88.

Referring now to FIG. 23, a thermally-transmissive portion of yet another embodiment of a flexible cryogenic structure is illustrated in a sectional view. In this embodiment an inner, apertured structure 100 has a flat wire 102 wrapped around it in a spiral manner. Thermally-transmissive segments 104 are disposed upon the wire 102 in a spaced-apart relationship, and a flexible, bio-compatible material 106 fills the interstices between segments 104. A thermocouple 108 can be associated with each segment 104. A wire 109 connects the thermocouple 108 to instrumentation near the proximal end of the structure. The exterior surface of the structure is smooth, and the structure can include 3 to 12 segments 104. In an exemplary embodiment the inner structure 100 is made of PTFE, the material 106 is 33 D Pebax, and the wire 102 is stainless steel or Nitinol. An apertured inner passage (similar to that shown in FIG. 21) is placed within the structure.

Figure 24:
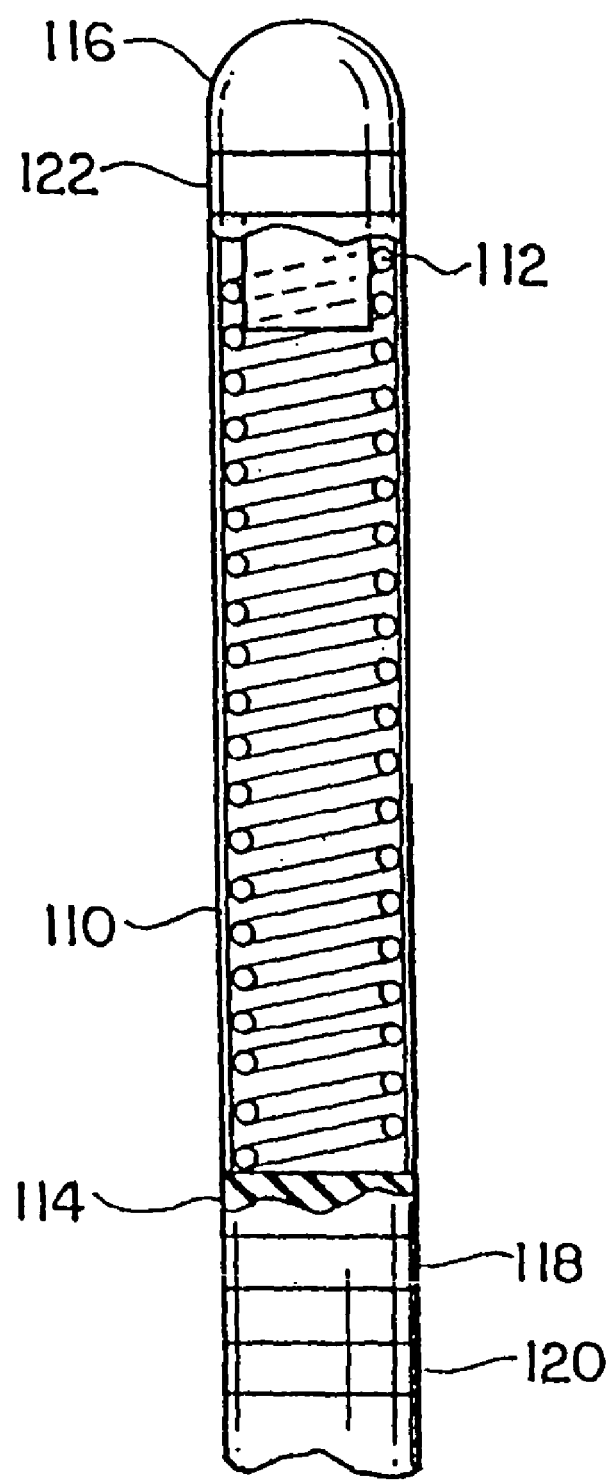
FIG. 24 depicts still another catheter embodiment.

FIG. 24 illustrates still another embodiment of a cryogenic cooling structure that includes a surface or wall 110 including a polymer or elastomer that is thin enough to permit thermal transfer. For example, polyamide, PET, or PTFE having a thickness of a typical angioplasty balloon or less (below 0.006 inches) provides acceptable thermal transfer. However, the thinness of the wall 110 allows it to readily collapse or otherwise deform under vacuum or near vacuum conditions applied to evacuate fluid/gas from the structure. Accordingly, the structure is provided with one or more supporting elements 112 such as a spring. The cooling structure is illustrated in association with a catheter 114 having a closed distal tip 116 and mono or bipolar ECG rings 118, 120, 122. The thermally-transmissive region is approximately 30 mm in length and is effective for thermal transfer over its entire circumference. However, as illustrated in FIG. 11, the thermally-transmissive region can be confined to specific region(s) of the device's circumference.

Figure 25:
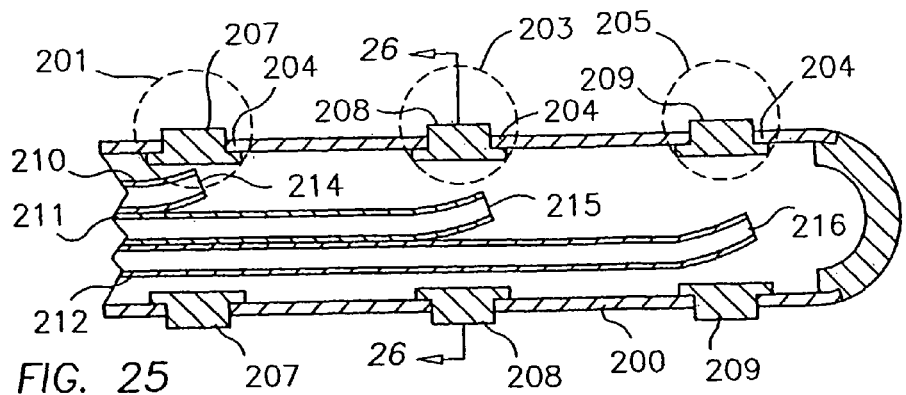
FIG. 25 illustrates yet another embodiment of the catheter.

Referring now to FIG. 25, an embodiment of the catheter is illustrated having three flexible members or injection tubes 210, 211 and 212 disposed within a first or outer flexible member 200. In an exemplary embodiment, the inner flexible members 210, 211 and 212 are arranged in a staggered configuration within the outer flexible member 200. As used herein, term "staggered" may be used to designate both a linearly/axially staggered configuration or alternatively, a rotationally staggered configuration. The flexible members 210, 211 and 212 thus define multiple staggered fluid paths within the outer member 200. In such a configuration, the injection tubes 210, 211 and 212 allow for greater aggregate cooling power as well as the creation of a variety of different cooling/freeze zones 201, 203 and 205 along the length of the outer flexible member 200. In an exemplary embodiment, thermocouples 204 disposed along the outer surface of the outer flexible member 200 may be integrated with an internal feedback loop to provide independent and variable regulation of these freeze zones.

Figures 26, 29, 30:
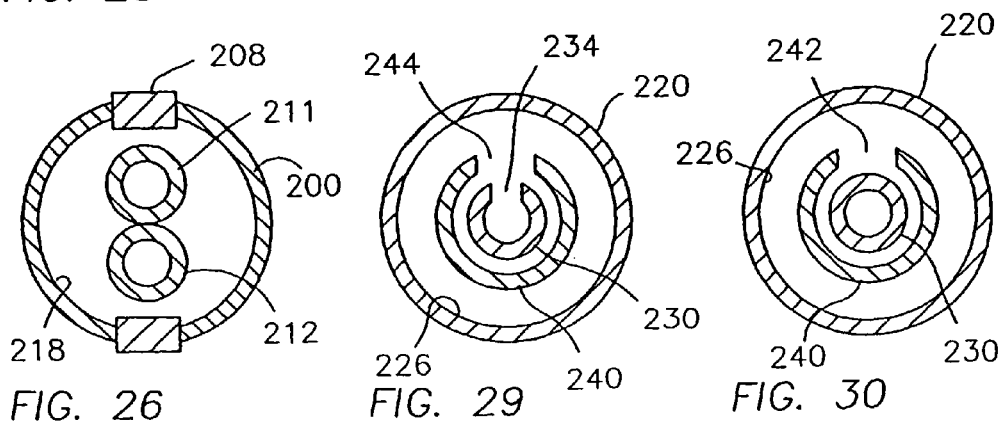
FIG. 26 is a sectional view of the catheter of FIG. 25 taken along line 26-26.
FIG. 29 is a sectional view of the catheter of FIG. 28 taken along line 29-29.
FIG. 30 is a sectional view of the catheter of FIG. 28 taken along line 30-30.

In an exemplary embodiment, the first inner member 210 includes at least one opening 214 positioned proximate an electrode ring member 207. Cryogenic fluid is expelled from the opening 214 and returns to the proximal end of the catheter along a fluid path defined by the inner wall 218 of the outer member 200, as shown in FIG. 26. Similarly, the second inner member 211 includes at least one opening 215 positioned proximate a second electrode ring member 208. Cryogenic fluid is also expelled from the opening 215 and returns to the proximal end of the catheter along the fluid path defined by the inner wall 218 of the outer member 200. Similarly, the third inner member 212 includes at least one opening 216 positioned proximate a third electrode ring member 209.

Alternatively, the catheter can be provided with only two inner members, or four or more inner members, not shown, disposed within the outer member. The inner members would have one or more openings proximate to and/or aligned with the inner face of one or more transmissive elements, as described earlier herein, to achieve different regions of freeze zones across the entire elongate member. Alternatively, all the staggered inner members may be simultaneously provided with cryogenic fluid to create a linear lesion for selected applications. The flow of cooling fluid along the fluid paths through the flexible members can also be alternated in any number of patterns among the multiple inner members to provide a desired cooling pattern such as a discontinuous or a continuous lesion across the entire catheter.

In an exemplary embodiment, a catheter with a plurality of thermally conductive electrode rings would have an underlying injection tube or tubes controlling the release of cryogenic fluid to each electrode. Such a catheter could be placed in the coronary sinus or endocardially along the atrioventricular junction. Once positioned, an electrogram of interest is located using a specific electrode ring on the catheter. Cold-mapping may be performed on the selected location to confirm the correctness of the location. Once confirmed, the area is cryoablated using the same electrode ring. The same embodiments and others described herein are equally suited to other organs besides the heart and/or any body portion that would benefit from the application of thermal energy.

Figure 27:
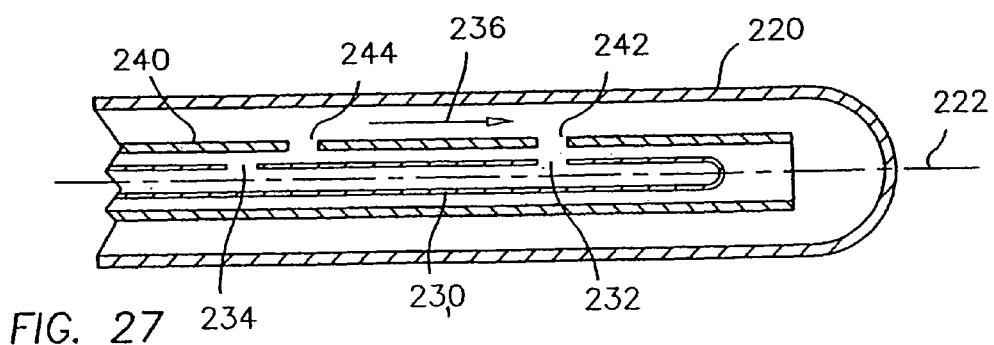
FIG. 27 illustrates yet still another embodiment of the catheter.

Referring now to FIG. 27, an embodiment of the catheter is illustrated having an outer member 220 with a fixed injection tube 230 disposed within a slidable sheath or overtube 240 therein. The injection tube and overtube are shown spaced apart for illustrative purposes only. Preferably, the injection tube is sized so that an outer surface of the injection tube engages an inner surface of the overtube while still allowing one member to slide or rotate relative to the other.

The fixed injection tube 230 has multiple openings 232, 234 formed thereon and the slidable overtube also has multiple openings or ports 242, 244 formed thereon. In one configuration shown in FIG. 27, opening 232 on the injection tube 230 coincides or is aligned with opening 242 on the slidable overtube 240. Thus, any fluid exiting the injection tube 230 from opening 232 is able to escape through opening 242.

Figure 28:
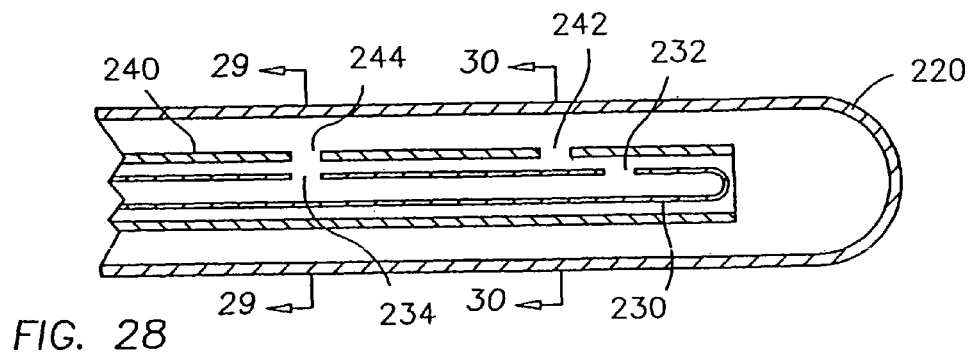
FIG. 28 illustrates the catheter of FIG. 27 in a second configuration.

As the slidable overtube 240 is slid or moved in a first direction as shown by arrow 236 along longitudinal axis 222, opening 232 is covered or blocked by the surface of overtube 240 as now shown in FIG. 28. In a second configuration shown in FIG. 29, opening 234 of injection tube 230 is aligned with opening 244 of overtube 240. In the same configuration, as shown in FIG. 30, opening 242 is not aligned with any opening formed on the surface of injection tube 230. Although only shown in two positions or configurations, the slidable overtube is positionable in any number of positions relative to the fixed injection tube. The overtube may also be used to partially-cover the openings on the injection tube to provide for a limited or controlled flow of cryogenic fluid.

Depending on which opening of the injection tube is aligned with the openings formed on the overtube, cryogenic fluid is expelled from the opening and returns to the proximal end of the catheter along a fluid path defined by the inner wall 226 of the outer member 220. The non-aligned opening will not expel fluid since the opening will be blocked. Alternatively, the injection tube and overtube can be provided with three or more openings to achieve multiple cooling/freeze zones along the length of the catheter.

Figure 31:
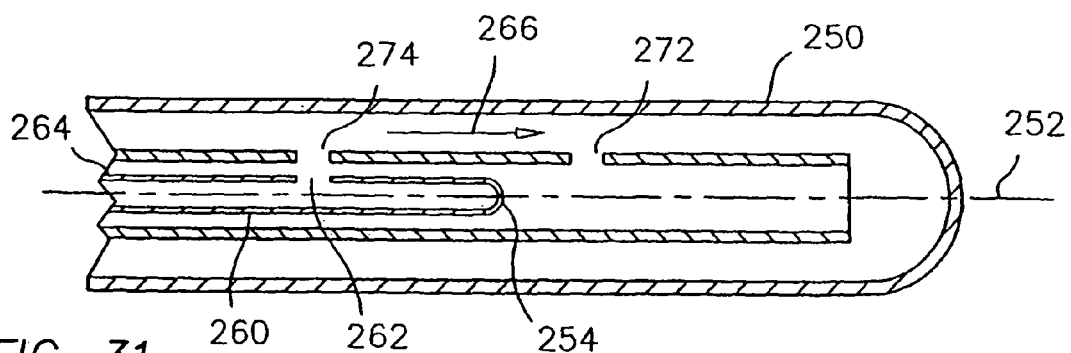
FIG. 31 illustrates yet another embodiment of the catheter.

Referring now to FIG. 31, an embodiment of the catheter is illustrated having a slidable injection tube 260 disposed within a fixed sheath or overtube 270. As shown in FIG. 31, both the injection tube 260 and overtube 270 are disposed within a flexible outer member 250. The slidable injection tube 260 has multiple openings 262, 264 formed thereon which allows for the release of cryogenic fluid. The fixed overtube 270 also has multiple perforations or openings 272, 274 formed thereon which allows for the differential release of fluid as described in more detail below. The injection tube may be further provided with a thermistor 254 disposed proximate the distal end of the tube to provide thermistor feedback. In one embodiment, the openings can be controlled by miniaturized means such as micro or nanovalves.

In a first configuration shown in FIG. 31, opening 262 of the injection tube 260 coincides or is aligned with opening 274 of the fixed overtube 270. As the slidable injection tube 260 is slid or moved in a first direction as shown by arrow 266, opening 262 is then aligned with corresponding opening 272 on the overtube 270 in FIG. 32.

Figure 32:
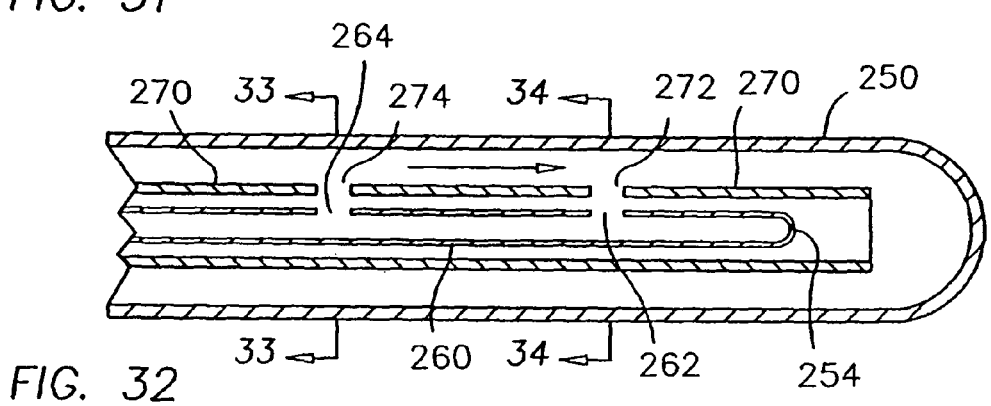
FIG. 32 illustrates the catheter of FIG. 31 in a second configuration.
Figure 33:
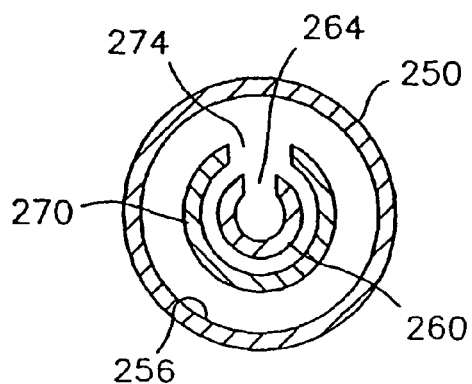
FIG. 33 is a sectional view of the catheter of FIG. 32 taken along line 33-33.
Figure 34:
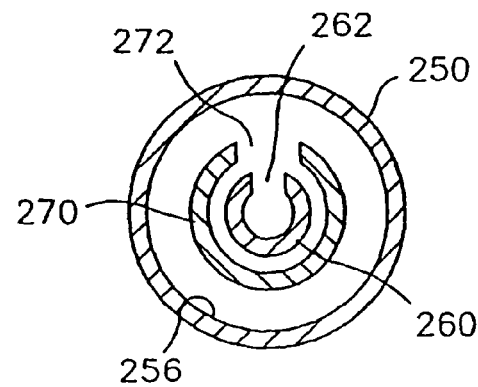
FIG. 34 is a sectional view of the catheter of FIG. 32 taken along line 34-34.

In this second configuration, as shown in FIGS. 32-34, openings 262, 264 of injection tube 260 are aligned with openings 272, 274 of overtube 270. Although only two configurations for the catheter are shown, the injection tube 260 is positionable in any number of locations relative to the fixed overtube 270.

In operation, cryogenic fluid is expelled from the openings and returns to the proximal end of the catheter along a fluid path defined by an inner wall 256 of the outer member 250. Alternatively, the injection tube 260 and overtube 270 can be provided with multiple openings proximate to and/or aligned with the inner face of one or more thermally-transmissive elements as described earlier herein to achieve more uniform cooling across the entire elongate, thermally-transmissive region.

Figure 35:
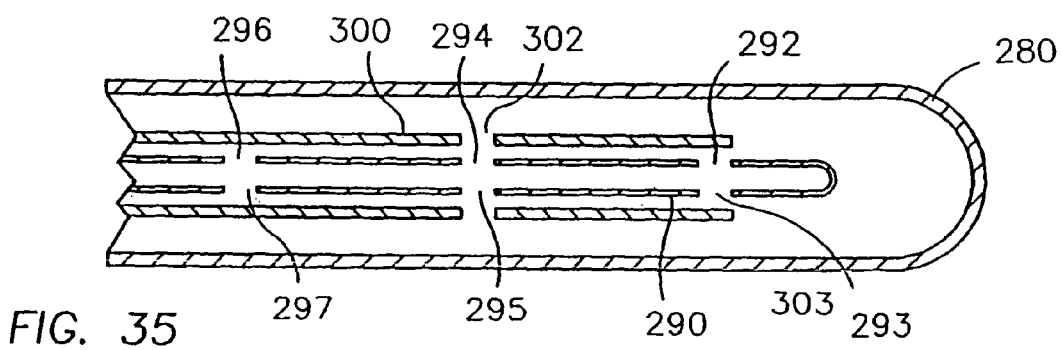
FIG. 35 illustrates yet another embodiment of the catheter.

Referring to FIG. 35, an embodiment of the catheter is illustrated having an outer member 280 with an injection tube 290 with multiple opposed openings 292-297 formed therein. Either the injection tube 290 or the overtube 300 may be slidable in a longitudinal plane to expose and/or cover one or more of the opposed openings on the injection tube 290. For example, as shown in FIG. 35, openings 294, 295 formed on the injection tube 290 are aligned with openings 302, 303 formed on the overtube 230. Furthermore, the injection tube may be positioned in a forwardmost position, not shown, to expose openings on the injection tube proximate the tip of the catheter. In this configuration, the injection tube would provide fluid to cool the area around the tip of the catheter.

In the embodiments described and shown above in FIGS. 32-35, electrode rings as shown in FIG. 25 may be provided along the outer surface of any of the outer members. The electrodes would serve both as electrical conductors and as a thermal transmitter at each location.

Figure 36:
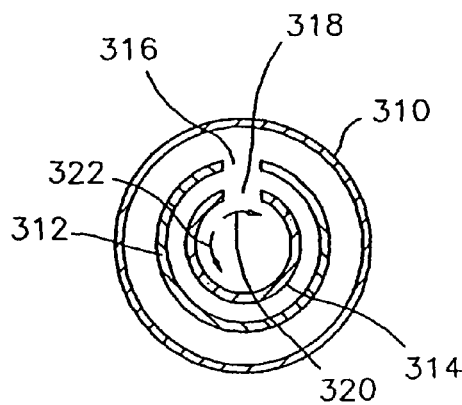
FIG. 36 is a sectional view of yet another embodiment of the catheter.
Figure 37:
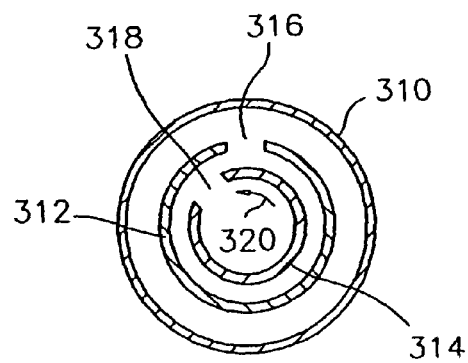
FIG. 37 is a sectional view of the catheter of FIG. 36 after rotation.

Referring to FIGS. 36 and 37, an embodiment of the catheter is illustrated have one or more rotatable members disposed within a flexible outer member 310. In this embodiment, the catheter includes an overtube member 312 and an injection tube member 314, one or both of which are rotatable with respect to one another. In an exemplary embodiment as shown in FIGS. 36 and 37, the injection tube 314 is rotatable relative to the fixed overtube 312. The injection tube 314 may be rotatable in either or both a clockwise and counterclockwise direction as indicated by arrows 320 and 322. As shown in FIG. 36, in a first configuration, opening 316 formed on the overtube 312 aligns with an opening 318 formed on the injection tube 314. As the injection tube 314 is rotated in a counterclockwise direction, the opening 318 on the injection tube 314 is placed out of alignment with the opening 316 formed on overtube 312, as shown in FIG. 37. Alternatively, the injection tube 314 may be fixed in the catheter while the overtube 312 is rotatable. In another embodiment, both the injection tube and overtube may both be rotatable. In yet a further embodiment, the injection tube and/or the overtube are rotatable and slidable within the outer member.

Figure 38:
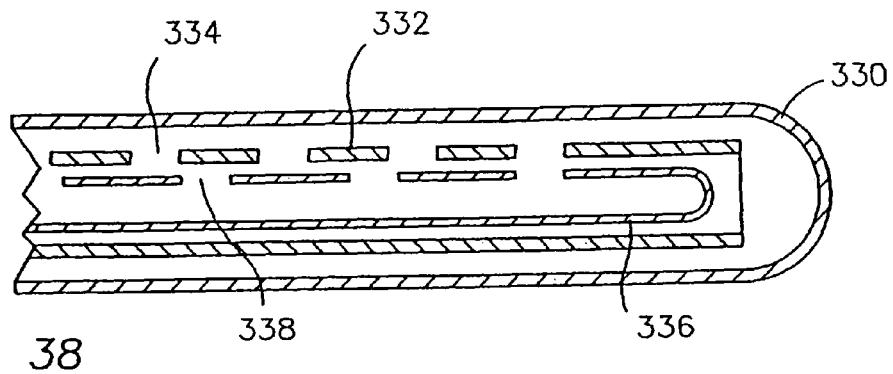
FIG. 38 illustrates yet another embodiment of the catheter.
Figure 39:
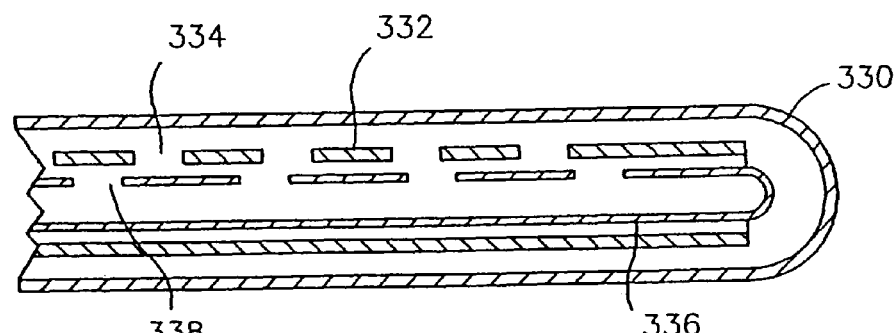
FIG. 39 illustrates the catheter of FIG. 38 in a second configuration.

In the embodiments shown and described above, the slidable and rotatable inner and outer tubes may have openings so arranged as to allow the fluid releasing openings to be in a variety of open and closed configurations with a minimum of relational movement between the tubes. For example, as shown in FIG. 38, an outer member 330 has disposed therein one slidably disposed inner tube 336 which has openings 338 formed thereon in a constant sequence, and a matching slidably disposed outer tube 332 which has openings 334 formed thereon in a constant sequence of slightly different length or intervals. In this configuration, as shown in FIG. 39, small linear relational movements bring the openings on the outer tube 332 and the inner tube 336 into an overlapping configuration.

In addition, the openings as shown and described herein may be so shaped as to allow additional control of fluid release. For example, an outer hole could be tear-shaped and match up with an inner opening that is tear-shaped rotationally aligned 180° oppositely (not shown). As the two narrow ends begin to overlap with slidable motion, a tiny aperture is created. With further slidable motion in the same direction, larger areas of the two openings overlap and larger volumes of cryogenic fluid can be released.

A variety of modifications and variations of the present invention are possible in light of the above teachings. Specifically, although many embodiments are illustrated being slender and flexible, other embodiments may be thick and rigid, and introduced into the body directly through incisions or through structures such as trocars. The opening and closing of the catheter openings may also be controlled by using nanotechnology and miniaturized valving. Furthermore, although some of the illustrated devices are particularly well suited for cardiac procedures, the same embodiments and others are equally suited to other organs and/or any body portion that would benefit from the application of thermal energy. For example, the illustrated devices may be used for treating arteries for restenosis or portions of the GI tract to stop bleeding or portions of the GU tract to treat spasm, inflammation, obstruction or malignancy. Thus, the devices as shown are not to be limited to catheters but should be viewed more broadly as cryogenic structures or portions thereof. All references cited herein are expressly incorporated by reference in their entirety.

As used herein, the term "target region" or "focus" shall mean a defined surface area, volume or mass of tissue, either in the heart or some other part of the human body. As used herein, the term "cryotreatment" shall mean the application of cold temperatures to cool body tissue, and shall include "cryoablation", which shall mean the application of cold temperatures to cool body tissue to such a degree so as to cause cell death, necrosis, or apoptosis in said tissue, or to otherwise surgically remove such tissue. Accordingly, as used herein, the term "treating" shall mean cooling or ablating. As used herein the term "catheter" shall include any medical instrument having a flexible or malleable body with a thermally transmissive region at the tip. Such an instrument may be used in numerous medical procedures including, but not limited to, surgical and intravascular procedures.

As used herein, the term "mapping" shall mean the use of medical imaging and other diagnostic techniques to measure and monitor body functions and physiological parameters, such as electrical activity in tissue. As used herein, the term "remapping" shall mean conducting mapping after an initial round of mapping and some ancillary diagnostic or surgical procedure has been initiated, as also used to describe the process of "progressive mapping", which shall mean the use of mapping in conjunction with a surgical procedure, as may be done in real time.

Cryotreatment entails creating cold temperatures at specific regions of the body or applying cold objects to tissue. Such "cold energy" can be safely and effectively used to treat a host of medical conditions by creating endothermic heat transfer from a surgical tool relative to a region of tissue, so as to induce hypothermia and cause such tissue to be cooled. Unlike heat-based technologies that destroy tissue structure, the application of cryotreatment preserves structural integrity. This benefit is achieved by selectively destroying the cellular components through intra-and inter-cellular ice formation while leaving the connective tissue matrix intact. In addition, cryotreatment shows potential to greatly minimize one of the most harmful side effects of heat-based treatments: thrombosis, or blood clot formation, which can lead to stroke. As a further advantage, cryotreatment affords the clinical practitioner effective and precise control of multiple operating parameters, such as iceball position, shape, size, and growth rates, tissue temperature, and cooling duration.

The cooling of tissue may be accomplished by disposing a cooling element or thermally transmissive segment proximate the focus tissue. The element or segment may be fitted onto or incorporated within or as part of a variety of medical instruments. For applications that require minimally invasive techniques, the cooling element or thermally-transmissive segment may be part of a slender catheter, which may then be positioned through heart vasculature near or at the situs of tissue to be cooled. The catheter may include one or more lumens or fluid paths, adapted to contain the flow of a liquid or gaseous fluid refrigerant therein. The fluid refrigerant is thereafter thermodynamically manipulated inside a "cryochamber." A cryochamber may be generally described as a defined, enclosed volume within the catheter, whereby, for example, the refrigerant flow may be expanded from high to low pressure, such as through a Joule-Thomson throttling process, to create endothermic heat transfer with respect to its surroundings. This heat transfer, when spatially directed to a target region of tissue will act to cool the tissue by absorbing heat from the tissue into the cryochamber and flow of refrigerant therein. The cryochamber is preferably thermally transmissive, having structural components that readily conduct heat. The cryochamber may also be electrically conductive, having elements that readily conduct electric charge. Examples of materials preferentially used to construct such a cryochamber are polymers, plastics, non-ferrous metals such as gold or copper, or a mixture thereof.

The refrigerant used may be any number of fluids suitable for stable compression to pressures on the order of 10 psig to up to 6000 psig. Some examples of such fluids are nitrous oxide ($N_2O$), nitrogen ($N_2$), argon, or AZ-20. Catheters may be flexible or rigid, constructed of a variety of materials, including plastics and both ferrous and non-ferrous metals, and would preferably have diameters on the order of 2 to 7 French.

Cryoablation recently became available through elongated and flexible catheters with different cooling element or segment configurations. Focal tips allow the destruction of a focal tissue area while a linear cooling segment allows the destruction of linear and elongated tissue structure. The natural properties of cryoablation, which include cryoadhesion, allow the cryoprobe to adhere to the heart tissue as it is cooled, thereby assuring the physician of precise positioning and secure lesion formation, particularly in a beating heart. Cryoablation allows cardiac ablation with minimal or no collateral damage related to coronary arteries restriction, pulmonary arteries, phrenic nerves and esophagus.

The present invention provides methods and devices for minimally invasive access to the pericardial space using the sub-xyphoid approach for performing epicardial cryomapping and cryoablation procedures or using a small thoracotomy approach in the chest wall to enter the pericardial space. For example, epicardial ablation can be performed using catheters, which are deflectable as well as flexible catheters that have a focal tip, linear, curved or inflatable cooling segment.

The present invention also allows for guiding the medical instrument by use of visualization, imaging and dissection techniques, including, for example, fluoroscopy imaging in an intravascular procedure and video thoracoscope in a minimally invasive surgical procedure. The visualization, imaging and dissection devices may assist in positioning the medical instrument in the targeted region of the tissue for cryotreatment.

Several techniques can be employed to achieve percutaneous access into the normal pericardial sac. In a first technique, the pericardial space can be entered through a sub-xyphoid puncture technique using the same 17-Gauge Tuohy needle that is used to enter the epidural space when administering epidural anesthesia (typically ~100 mm overall length, and 1.5 mm O.D.). Sub-xyphoid incisions are typically less than 10 centimeters in length. As the needle approaches the heart under fluoroscopic guidance, small amounts of contrast media are injected to document penetration of the needle tip into the pericardial space. Proper positioning of the needle is associated with layering of the contrast in the pericardial space. Once this space is entered, a guide wire is passed through the needle. A standard introducer sheath, and subsequently an ablation catheter are passed into the pericardial space.

In a second technique, a catheter system can be employed in a percutaneous approach from the femoral vein to pierce the right atrial appendage. In this technique, a small perforation is made in the right atrial appendage using a custom-fabricated, 21-gauge, hollow, radiopaque needle mounted at the tip of a 4F catheter. A soft, 0.014 guidewire with a second radiopaque marker is then advanced through the needle and catheter into the pericardial space to secure the point of entry, guide the application catheter, and confirm its position in the pericardial space.

For a third approach, a device having a 21-gauge needle housed within a 12-Fr stainless steel tube of 20 cm in length is percutaneously inserted into the anterior mediastinal space until its distal tip is in contact with the anterior aspect of the pericardial sac. Negative pressure is applied using a vacuum syringe to capture the pericardium into the hemispheric cavity. Thus, when a needle is advanced to puncture the pericardial bubble, there is minimal risk of damage to the cardiac structures.

In a fourth approach, one or more small thoracotomy incisions are made in the chest wall between the ribs to permit access for thoracoscopic instruments and cameras, which provide dissection and visualization capabilities in the pericardial space for insertion and manipulation of medical instruments. The small thoracotomy incisions are typically less than 10 centimeters in length. In this approach, the decompression of the pleural space may be necessary in order to achieve pericardial access. During all the above procedures, the medical instrument is actuated externally to the chest cavity.

As discussed, arrhythmia-causing tissue involved in AF and VT or other arrhythmia can be located on the endocardial surface of the heart, the epicardial surface or in the myocardium. Thus, the present invention foresees the use of minimally invasive epicardial mapping and/or ablation procedures combined with traditional endocardial mapping and/or ablation procedures to effectively localize and destroy the aberrant electrical tissue.

Another application for such methods and devices is to perform ablation to treat aortic cusp VTs. Patients with these types of VTs tend to have no other underlining arrhythmias and therefore present a significant potential for destroying coronary structure when RF energy is used.

Figure 40:
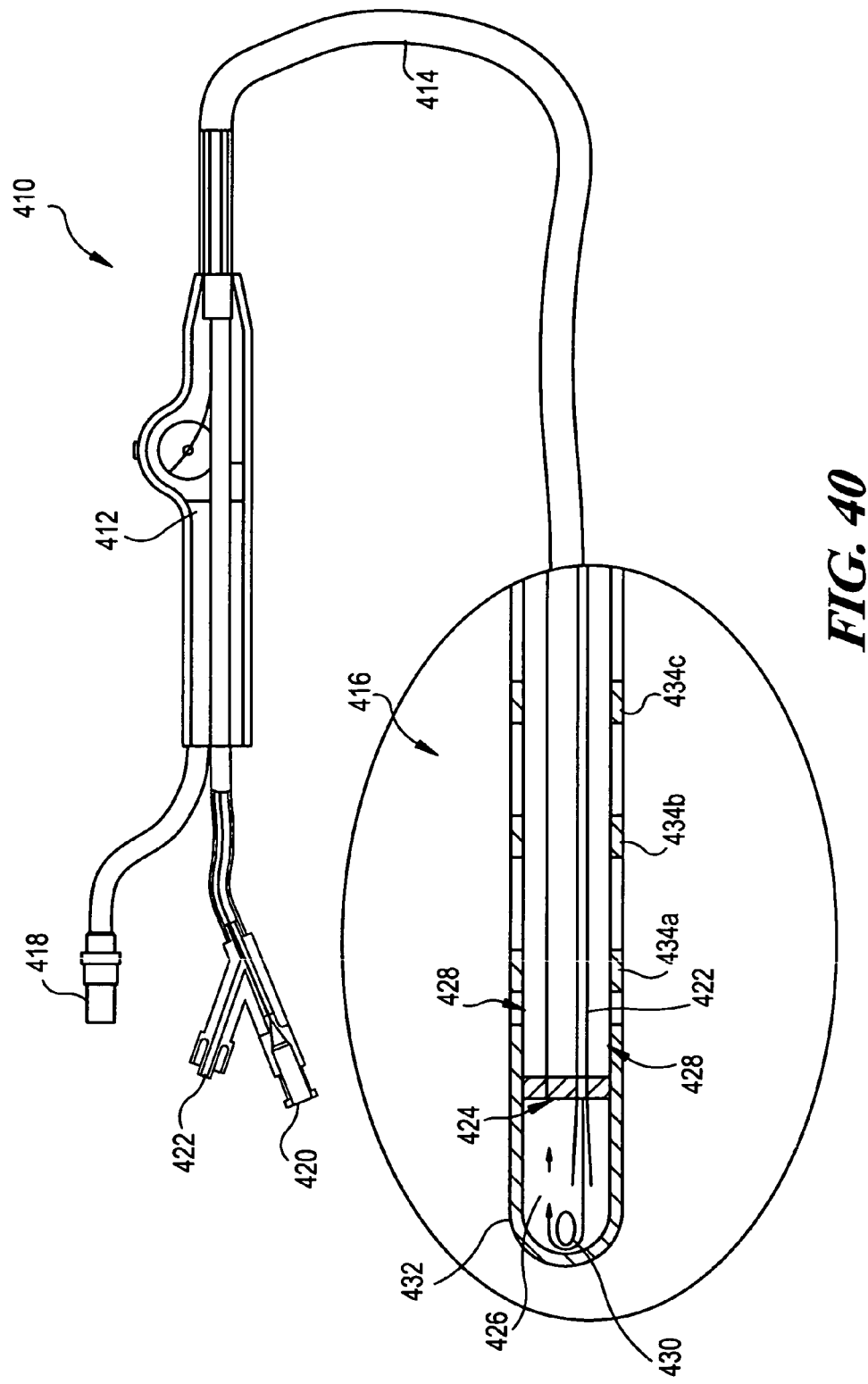
FIG. 40 is a diagram illustrating an exemplary medical instrument for use in a cryotreatment of a target region or ablation location.

FIG. 40 shows a catheter 410 used in a system in accordance with the present invention. As shown, the handle 412 is equipped with input ports for an electrical connector 418, a coolant injection tube connector 420, and a return tube connector 422. These connect via various internal junctions or tubes passing through the handle to provide these three functions to the distal tip of the catheter. The handle 412 may also include various control assemblies, e.g., switches or valves, as well as safety detection or shut down elements (not illustrated).

Leading from the handle 412 is an elongated catheter body 414 that extends to the catheter tip 416, illustrated in enlarged detail to show a representative structure thereof. As shown in catheter tip 416, the coolant enters through a central tube 422 and exits via a nozzle 424 at the end of the tube to expand in a contained region forming a chamber 426 at the tip of the catheter. In the illustrated construction, the tube 422 runs concentrically within an outer tube (not numbered) thereby forming an annular return space 424 surrounding the supply tube 422 and extending back to the fluid return connector 422 of the handle. As discussed further below, the return passage for expended coolant is a vacuum passage, thus assuring that leakage into the blood stream cannot occur.

The location of chamber 426 defines the cooling region of the catheter tip. In the illustrated embodiment this is a short chamber less than a centimeter long located at the very tip of the catheter. Also shown are a thermocouple 430 positioned within the tip to sense tip temperature, and a plurality of electrodes including a tip electrode 432 and one or more ring electrodes 434*a*, 434*b* . . . which are positioned near the tip for use in mapping and/or detecting cardiac signals. In other embodiments, the chamber 426 defined at the tip of the catheter may be an elongated chamber several centimeters in length for defining a coolant chamber effective to form linear lesions when placed in contact with tissue such as the cardiac wall. For the linear embodiment, multiple expansion nozzles, a perforated inlet tube end segment, or other variation in the construction of the coolant supply line may be used to assure a high rate of cooling along the full length of the expansion chamber. Furthermore, the chamber wall may be very thin, or formed with a metal sleeve or cap to achieve high heat transfer rates. Other structures within the catheter may include torque or steering wires, or other elements conventional in the art for navigation of the catheter past branch points in vessels, and for urging the catheter tip into contact with a wall once its position is confirmed.

While not illustrated in FIG. 40, one or more electrical sensing elements in addition to the thermocouple may be provided at various places within the catheter to provide useful feedback or emergency control functions.

FIGS. 41-46 show the use of catheters constructed in accordance with the principles of the present invention for cryotreatment or cryoablation of epicardial tissue. In use, ablating a predetermined portion of epicardial tissue of a patient is accomplished by inserting a catheter having a tip portion into the patient, guiding the catheter to a predetermined portion of the patient's epicardial tissue and positioning the tip portion adjacent the predetermined portion of the patient's epicardial tissue to be ablated. The predetermined portion of the epicardial tissue adjacent the tip portion can than be ablated, preferably using cryoablation. The catheter can be any suitable catheter that can be arranged to contact the desired treatment location, for example, a flexible catheter, a semi-rigid catheter, a deflectable catheter, etc. The catheter can be arranged to have a cooling segment that may be, for example, a focal tip, a linear tip, a curved tip or an inflatable tip.

Figure 41:
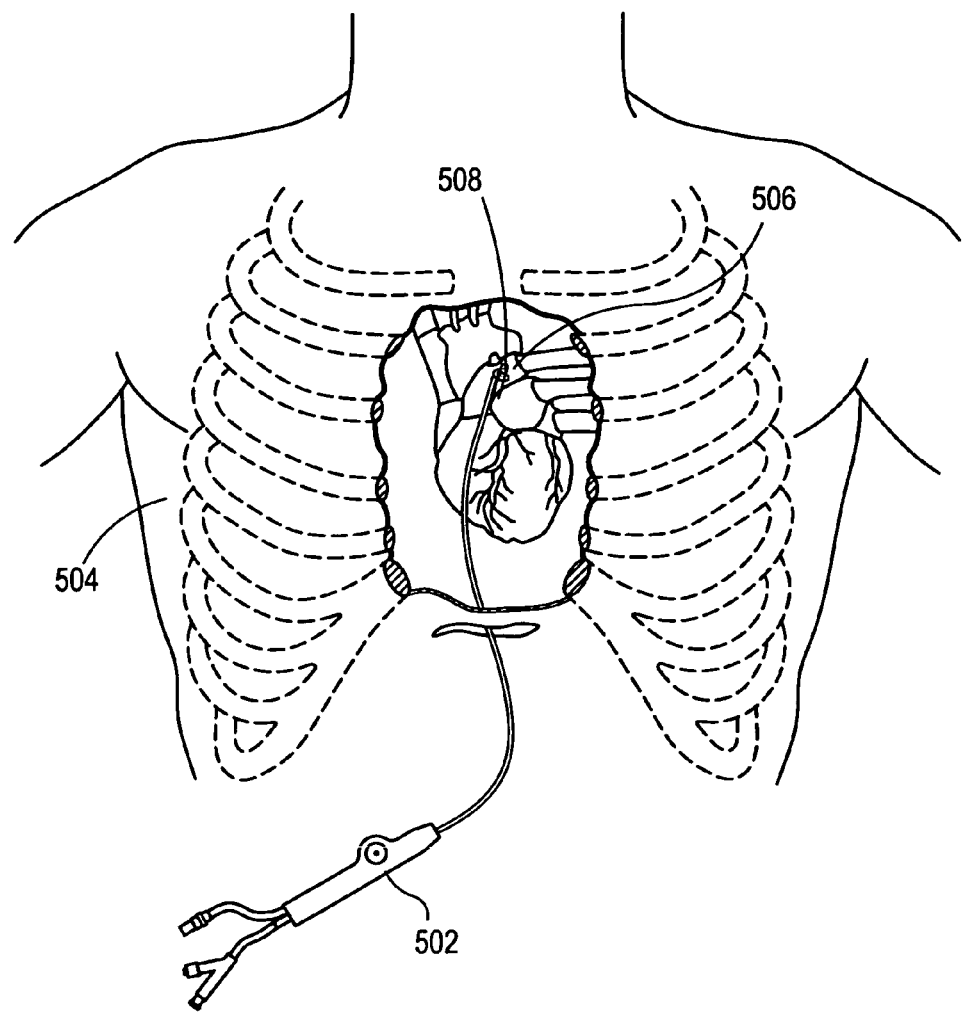
FIG. 41 is a diagram illustrating cryotreatment using a catheter arranged for encircling a target region or ablation location.
Figure 42A:
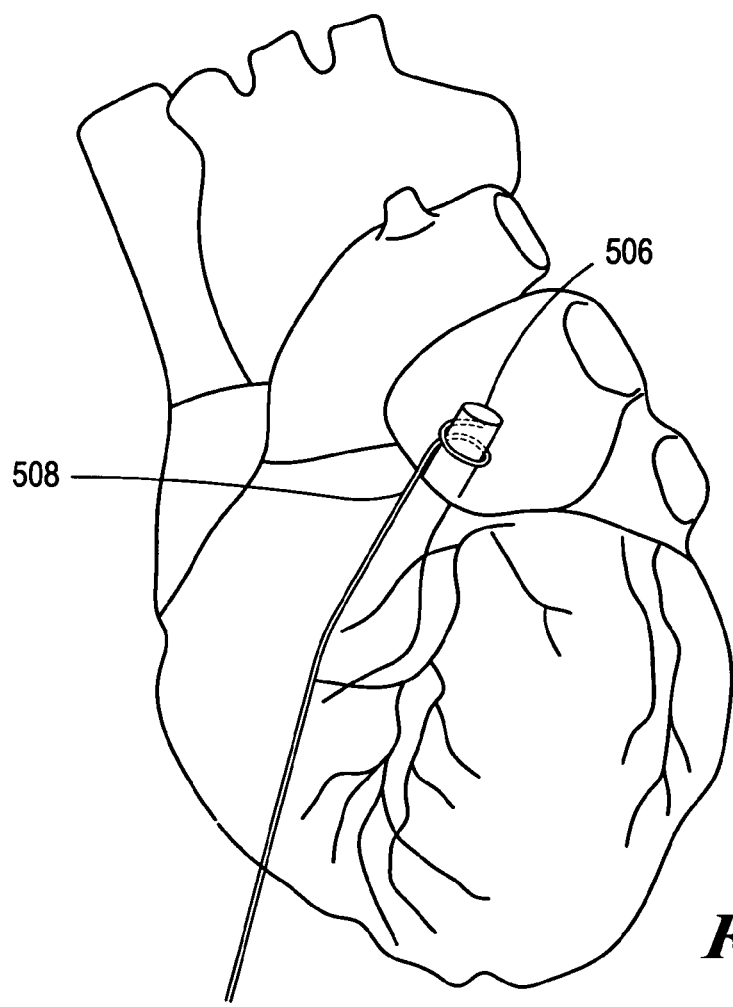
FIG. 42A is a diagram illustrating a more detailed view of the target region in contact with the cryotreatment element of FIG. 41.
Figure 42B:
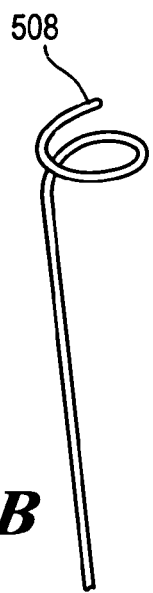
FIG. 42B is a diagram illustrating a more detailed view of the cryotreatment element of FIG. 41.

FIG. 41 illustrates an embodiment of one method by which a thermally transmissive device, such as a catheter 502 is inserted into the body of a patient 504 and guided to a target region of cardiac tissue 506. The catheter 502 contains a cryotreatment or cryoablation element 508 located at its distal tip which is positioned adjacent the target region of epicardial tissue 506. FIG. 42A illustrates a more detailed view of the target region of cardiac tissue 506 in contact with the cryotreatment element 508. FIG. 42B illustrates an exemplary embodiment of the cryotreatment element 508.

The cryotreatment element 508 further includes a cryochamber therein (not shown) whereby a flow of refrigerant fluid is thermodynamically manipulated or cycled to cool the surrounding environment, that being the target tissue region 506. An example of the thermodynamic process may be gas expansion through Joule-Thomson cooling, or evaporation of the refrigerant from liquid to gaseous phase, or both. It is readily understood that catheter 502 includes one or more lumens disposed along its length (not shown) which carry the flow of refrigerant from a source or supply coupled to the catheter's proximal end, to the cryotreatment element 508, and then back through the catheter, either in a closed loop arrangement where refrigerant is recycled through the system and recaptured, or an open loop system wherein refrigerant is vented from the system without recapture. For certain applications, an arrangement may be used where a substance, being preferably non-toxic or inert, is injected by the catheter into the tissue region 506. One example of such a use would be that of injecting drugs or other therapeutic agents either in conjunction with, or independent of, the cooling of tissue via the cryotreatment element 508.

As refrigerant flows through the catheter 502, and cooling is progressively applied, the size of the iceballs, and/or isotherms in the case of warmer, non-freezing cryotreatment, formed in and around the target tissue region 506 may grow in size. Such iceballs or isotherms may be circular nature, however it is readily understood that varying shapes may be formed, having linear, cylindrical, ellipsoidal, toroidal, or curved topologies.

The cooling of the target tissue 506 may either temporarily or permanently interrupt electrical activity proximate such tissue. The resulting effects on the heart may then be measured, as with the mapping techniques outlined above. This method may be incorporated into a "progressive mapping" scheme, whereby specific heart regions are mapped; cryotreatment is applied; the regions are again mapped or "remapped"; the effects of the cryotreatment are evaluated; and, if necessary, additional cycles of mapping and cryotreatment are executed until the desired results are achieved. Throughout the process, the tissue may be neither destroyed nor removed. In this sense therefore, cryotreatment and "cryomapping" allow for real-time, feedback oriented treatment of heart tissue, wherein such treatment is reversible and non-permanent.

Figure 43:
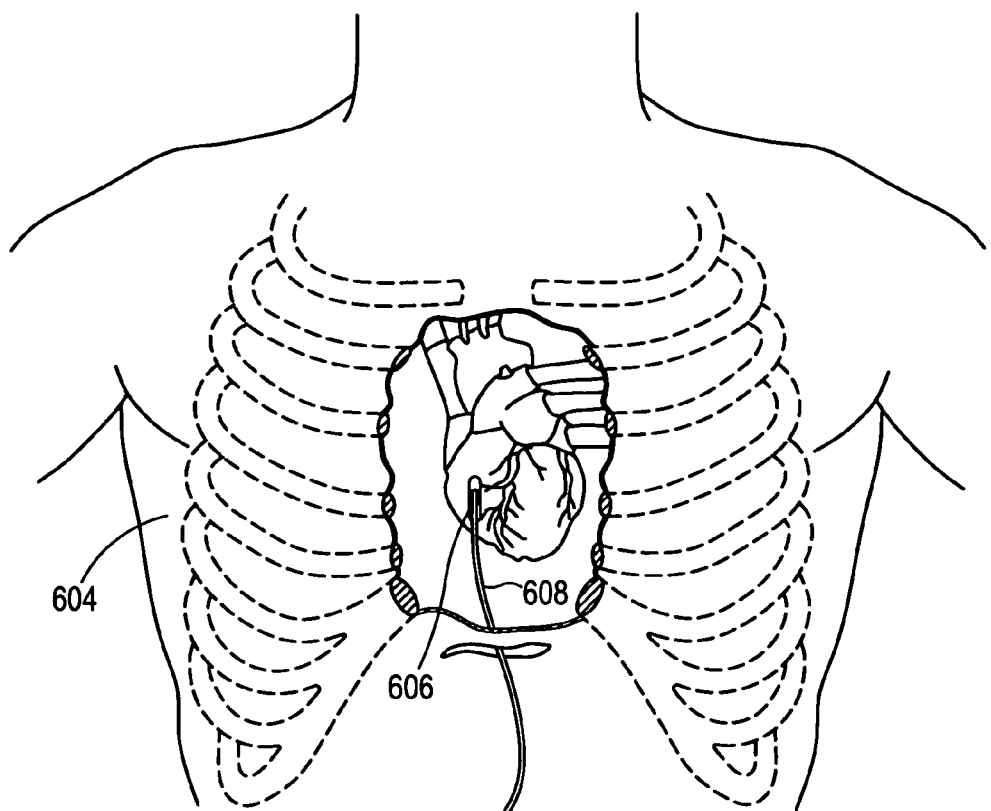
FIG. 43 is a diagram illustrating cryotreatment using a deflectable catheter arranged to contact a target region or ablation location.

FIG. 43 shows an alternative method by which a target region of cardiac tissue may be treated via cryotreatment. FIG. 43 illustrates an embodiment of one method by which a flexible catheter 602 is inserted into the body of a patient 604 and guided to a target region of epicardial tissue 606. The catheter 602 contains a cryotreatment or cryoablation element 608 located at its distal tip which is positioned adjacent the target region of epicardial tissue 606. The cryotreatment element 608 further includes a cryochamber therein (not shown) whereby a flow of refrigerant fluid is thermodynamically manipulated or cycled to cool the surrounding environment, that being the target tissue region 606. The catheter 602 is a flexible linear catheter arranged for contact with a target region of the linear and elongated epicardial tissue 606.

Figure 44:
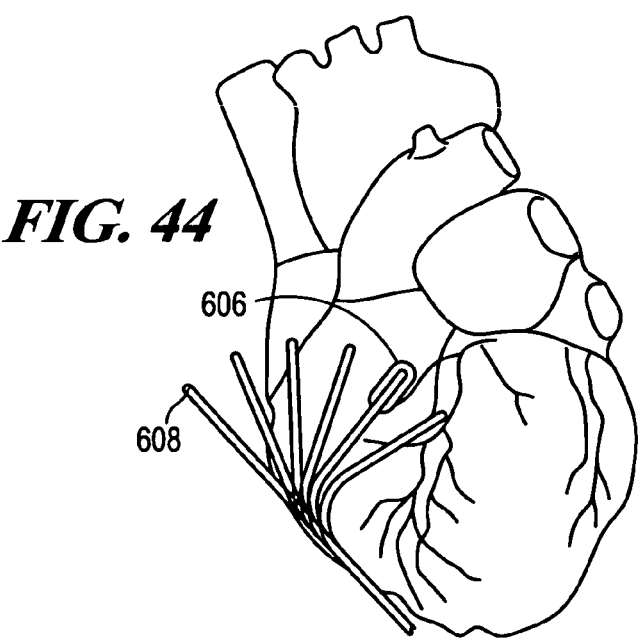
FIG. 44 is a diagram illustrating a more detailed view of the target region in contact with the cryotreatment element of FIG. 43.

FIG. 44 illustrates a more detailed view of the target region of cardiac tissue 606 and multiple positions of a flexible linear catheter cryotreatment element 608.

Figure 45:
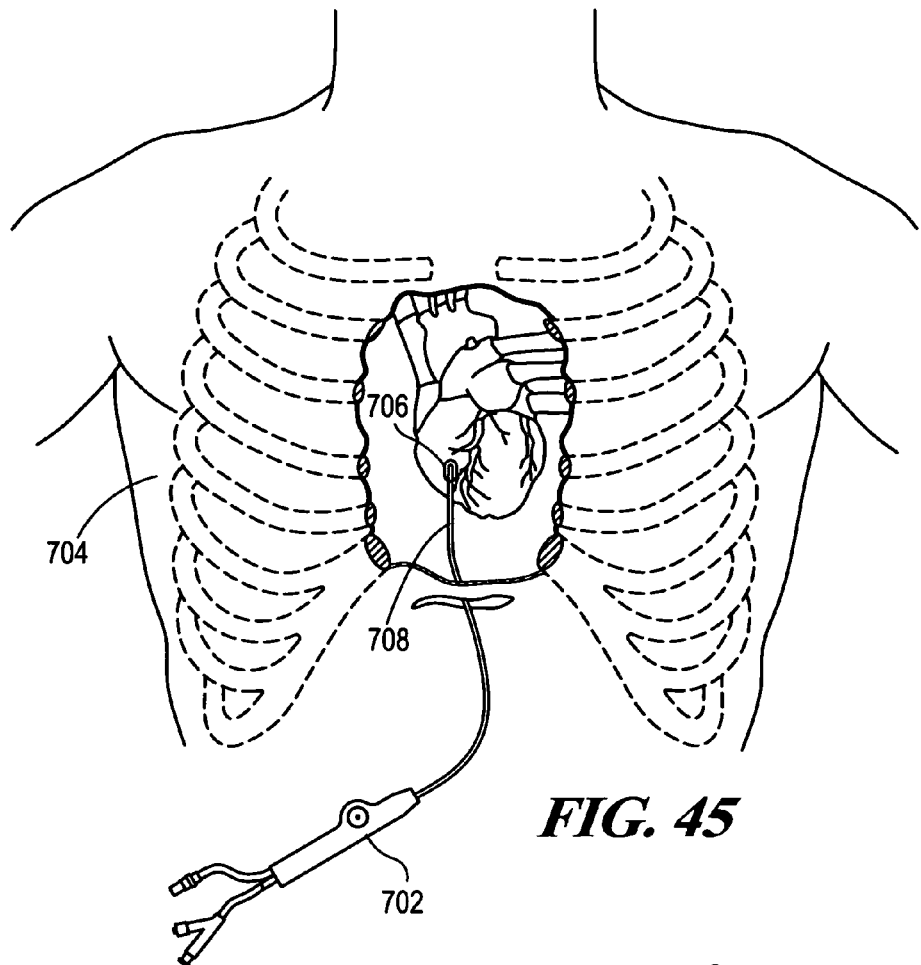
FIG. 45 is a diagram illustrating cryotreatment using a catheter arranged to contact a target region or ablation location.

FIG. 45 shows an alternative method by which a target region of cardiac tissue may be treated via cryotreatment. FIG. 45 illustrates an embodiment of one method by which a flexible catheter 602 is inserted into the body of a patient 704 and guided to a target region of epicardial tissue 706. The catheter 702 contains a cryotreatment or cryoablation element 708 located at its distant tip which is positioned adjacent the target region of epicardial tissue 706. The cryotreatment element 708 further includes a cryochamber therein (not shown) whereby a flow of refrigerant fluid is thermodynamically manipulated or cycled to cool the surrounding environment, that being the target tissue region 706. The catheter 702 is a deflectable linear catheter arranged for contact with a target region of the linear and elongated epicardial tissue 706.

Figure 46:
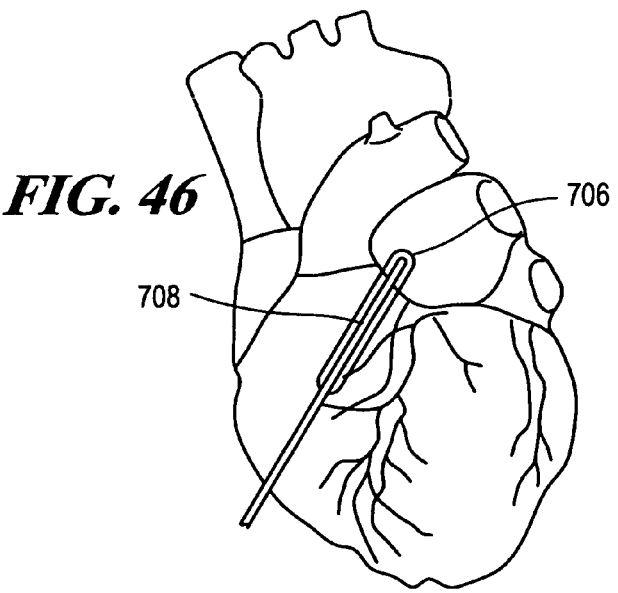
FIG. 46 is a diagram illustrating a more detailed view of the target region in contact with the cryotreatment element of FIG. 45.

FIG. 46 illustrates a more detailed view of the target region of epicardial tissue 706 in contact with a deflectable linear catheter cryotreatment element 708.

Cryotreatment as used the methods described above may generate a widely varying range of tissue temperatures. Tissue temperatures in the range of +30 to −40 degrees Celsius may be used to cause a reversible interruption of electrical activity in either normal or arrhythmic tissue. This range may also be used with mapping techniques to confirm the effects of cryotreatment and to assess heart function. Tissue temperatures in the range of +20 to −200 degrees Celsius may be used to cause permanent interruption of electrical activity, cell death, necrosis, or apoptosis in some or all of the tissues surrounding the target region of tissue.

Although the present invention has been described with respect to epicardial ablation, it is not limited to epicardial tissue. It should be understood by those of ordinary skill in the art that the device and method described herein may be used for the exterior ablation of numerous types of blood vessels as well.

It will be appreciated by persons skilled in the art that the present invention is not limited to what has been particularly shown and described herein above. In addition, unless mention was made above to the contrary, it should be noted, "all of the accompanying drawings are not to scale". A variety of modifications and variations are possible in light of the above teachings without departing from the scope and spirit of the invention, which is limited only by the following claims.

What is claimed is:

1. A method for ablating a target region of cardiac tissue, comprising the steps of:
    providing a medical instrument having
        a flexible body having
            at least one lumen,
            proximal and distal end portions, the distal end portion enclosing
                a thermally transmissive cryochamber in fluid communication with the at least one lumen;
                a thermally transmissive coil eccentric with respect to the flexible body and in fluid communication with the at least one lumen,
    positioning the instrument to dispose the cryochamber proximate the target region of cardiac tissue,
    injecting a cryogenic fluid flow into the at least one lumen in the instrument body,
    expanding the cryogenic fluid flow inside the cryochamber,
    controlling the flow of cryogenic fluid remote from the thermally-transmissive cryochamber to vary the temperature and rate of cooling of the cryochamber,
        wherein the step of positioning the instrument to dispose the cryochamber proximate the target region of cardiac tissue comprises:
        percutaneously inserting the distal end portion of the instrument through the pericardium for accessing the target region of cardiac tissue, and
        advancing the instrument through the pericardium to dispose the cryochamber proximate the target region of cardiac tissue; and
    sensing electrical activity of the cardiac tissue to be treated, wherein sensing electrical activity and ablating the tissue occur substantially simultaneously.

2. The method according to claim 1, wherein controlling the flow of cryogenic fluid comprises directing the fluid to the cryochamber through a first fluid flow passage formed in the instrument and removing the fluid by directing the fluid through a second fluid flow passage formed in the instrument.

3. The method according to claim 1, wherein the instrument is remotely actuated external to the chest cavity.

4. The method according to claim 1, further comprising throttling the flow of cryogenic fluid to provide reversible cooling of the tissue adjacent the cryochamber.

* * * * *